United States Patent
Yamamoto et al.

(10) Patent No.: US 10,388,876 B2
(45) Date of Patent: Aug. 20, 2019

(54) ORGANIC SEMICONDUCTOR COMPOSITION, PHOTOVOLTAIC ELEMENT, PHOTOELECTRIC CONVERSION DEVICE, AND METHOD OF MANUFACTURING PHOTOVOLTAIC ELEMENT

(71) Applicant: Toray Industries, Inc., Tokyo (JP)

(72) Inventors: Shuhei Yamamoto, Otsu (JP); Daisuke Kitazawa, Otsu (JP)

(73) Assignee: Toray Industries, Inc., Tokyo (JP)

( * ) Notice: Subject to any disclaimer, the term of this patent is extended or adjusted under 35 U.S.C. 154(b) by 156 days.

(21) Appl. No.: 15/516,492

(22) PCT Filed: Sep. 30, 2015

(86) PCT No.: PCT/JP2015/077720
§ 371 (c)(1),
(2) Date: Apr. 3, 2017

(87) PCT Pub. No.: WO2016/059972
PCT Pub. Date: Apr. 21, 2016

(65) Prior Publication Data
US 2018/0240977 A1  Aug. 23, 2018

(30) Foreign Application Priority Data
Oct. 14, 2014  (JP) .................. 2014-209703

(51) Int. Cl.
*H01B 1/12* (2006.01)
*H01L 51/00* (2006.01)
(Continued)

(52) U.S. Cl.
CPC .......... *H01L 51/0036* (2013.01); *C07C 43/20* (2013.01); *C07C 43/205* (2013.01);
(Continued)

(58) Field of Classification Search
CPC .......... C08L 65/00; C08K 3/045; C08K 5/01; C08K 5/06; C08K 5/07; C08K 5/15;
(Continued)

(56) References Cited

U.S. PATENT DOCUMENTS

2014/0042369 A1* 2/2014 Huang ................ H01L 51/0053
252/500
2014/0151657 A1 6/2014 Wang et al.
(Continued)

FOREIGN PATENT DOCUMENTS

EP 2 730 632 5/2014
JP 2004-126372 A 4/2004
(Continued)

OTHER PUBLICATIONS

Yongye Liang et al., "For the Bright Future—Bulk Heterojunction Polymer Solar Cells with Power Conversion efficiency of 7.4%," Advanced Materials, vol. 22, Issue 20, May 25, 2010, pp. E135-E138 (Abstract).
Supplementary European Search Report dated May 7, 2018, of corresponding European Application No. 15851594.0.

*Primary Examiner* — Mark Kopec
*Assistant Examiner* — Jaison P Thomas
(74) *Attorney, Agent, or Firm* — DLA Piper LLP (US)

(57) ABSTRACT

A photovoltaic element has high photoelectric conversion efficiency as well as excellent processing properties/low environmental load. The organic semiconductor composition includes as an additive a compound in which one or two aromatic rings are substituted with a predetermined number of alkyl groups, alkoxy groups, alkanoyl groups, or thioalkyl groups. There is also a method of manufacturing a photovoltaic element which uses the composition.

20 Claims, 1 Drawing Sheet

(51) Int. Cl.
| | |
|---|---|
| *C07C 43/20* | (2006.01) |
| *C07C 43/205* | (2006.01) |
| *C07C 321/28* | (2006.01) |
| *C07C 49/67* | (2006.01) |
| *C08L 65/00* | (2006.01) |
| *H01L 51/42* | (2006.01) |
| *H01L 51/44* | (2006.01) |
| *C08K 5/01* | (2006.01) |
| *C08K 5/06* | (2006.01) |
| *C08K 5/07* | (2006.01) |
| *C08K 5/15* | (2006.01) |
| *C08K 5/372* | (2006.01) |
| *C08K 3/04* | (2006.01) |

(52) U.S. Cl.
CPC ............ *C07C 49/67* (2013.01); *C07C 321/28* (2013.01); *C08K 3/045* (2017.05); *C08K 5/01* (2013.01); *C08K 5/06* (2013.01); *C08K 5/07* (2013.01); *C08K 5/15* (2013.01); *C08K 5/372* (2013.01); *C08L 65/00* (2013.01); *H01B 1/12* (2013.01); *H01L 51/0007* (2013.01); *H01L 51/0043* (2013.01); *H01L 51/0046* (2013.01); *H01L 51/4253* (2013.01); *H01L 51/442* (2013.01); *C08G 2261/124* (2013.01); *C08G 2261/146* (2013.01); *C08G 2261/149* (2013.01); *C08G 2261/1412* (2013.01); *C08G 2261/3223* (2013.01); *C08G 2261/3243* (2013.01); *C08G 2261/414* (2013.01); *H01L 51/0037* (2013.01); *H01L 2251/308* (2013.01); *Y02E 10/549* (2013.01); *Y02P 70/521* (2015.11)

(58) Field of Classification Search
CPC ....... C08K 5/372; C07C 321/28; C07C 43/20; C07C 43/205; C07C 49/67; C08G 2261/124; C08G 2261/1412; C08G 2261/146; C08G 2261/149; C08G 2261/3223; C08G 2261/3243; C08G 2261/414; H01L 2251/308; H01L 51/0007; H01L 51/0036; H01L 51/0037; H01L 51/0043; H01L 51/0046; H01L 51/4253; H01L 51/442; Y02E 10/549; Y02P 70/521; H01B 1/12

See application file for complete search history.

(56) References Cited

U.S. PATENT DOCUMENTS

| | | | |
|---|---|---|---|
| 2014/0190566 A1* | 7/2014 | Itoh | C07D 311/74 136/263 |
| 2015/0236288 A1* | 8/2015 | Nakano | H01L 51/426 136/263 |

FOREIGN PATENT DOCUMENTS

| | | | | |
|---|---|---|---|---|
| JP | 2013-058714 A | | 3/2013 | |
| JP | 2014-027176 A | | 2/2014 | |
| JP | 5482973 B1 | | 2/2014 | |
| JP | 2014027176 A | * | 2/2014 | |
| JP | 2014-189666 A | | 10/2014 | |
| WO | 2012/102390 A1 | | 8/2012 | |
| WO | 2014/042091 A1 | | 3/2014 | |
| WO | WO-2014069468 A1 | * | 5/2014 | ......... H01L 15/0036 |

* cited by examiner

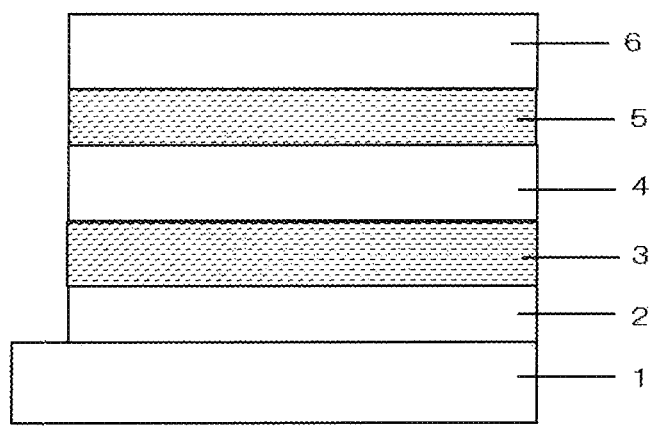

ORGANIC SEMICONDUCTOR COMPOSITION, PHOTOVOLTAIC ELEMENT, PHOTOELECTRIC CONVERSION DEVICE, AND METHOD OF MANUFACTURING PHOTOVOLTAIC ELEMENT

TECHNICAL FIELD

This disclosure relates to an organic semiconductor composition, a photovoltaic element using the same, a photoelectric conversion device and a method of manufacturing a photovoltaic element.

BACKGROUND

Solar cells have drawn public attention as an effective and environment-friendly energy source that can solve energy problems that have currently become more and more serious. At present, as a semiconductor material for use in photovoltaic elements for solar cells, inorganic substances such as monocrystalline silicon, polycrystalline silicon, amorphous silicon, and a compound semiconductor, have been used. However, since the solar cell to be manufactured by using inorganic semiconductors requires high costs compared to other power generation systems such as thermal power generation, it has not been widely used for general household purposes. The main reason for the high costs lies in that a process of forming a semiconductor thin-film requires high temperature and vacuum conditions. For this reason, organic solar cells have been investigated in which, as a semiconductor material expected to simplify the manufacturing process, an organic semiconductor and an organic dye such as a conjugated polymer and an organic crystal, are used. In such organic solar cells, the manufacturing process can be significantly simplified since the semiconductor material layer can be prepared by an application method.

However, the organic solar cells using the conjugated polymer or the like is lower in its photoelectric conversion efficiency than conventional solar cells using inorganic semiconductors and, therefore, those solar cells have not been put into practical use. To put the organic solar cell into practical use, it is essential to further improve photoelectric conversion efficiency.

As a method of improving the photoelectric conversion efficiency of the organic solar cell, a method in which when a photoelectric conversion layer composed of an electron donating organic semiconductor (e.g., a conjugated polymer) and an electron accepting organic semiconductor (e.g., a fullerene compound) is applied and formed, the photoelectric conversion layer is applied and formed by adding 1,8-diiodooctane to a solvent as an additive without using a single solvent, is often used (e.g., "Advanced Materials," Vol. 22, p. E135-E138, 2010 and JP 5482973 B1).

When applying/forming a photoelectric conversion layer composed of the electron donating organic semiconductor and the electron accepting organic semiconductor, it is thought that the phase-separation structure is affected by affinity/repulsive properties among the electron donating organic semiconductor, the electron accepting organic semiconductor, a solvent and an additive, and is determined while these have complicated effects on one another. We believe that among the affinity, the affinity between the electron accepting organic semiconductor and the solvent, and the affinity between the electron accepting organic semiconductor and the additive are particularly important.

When the photoelectric conversion layer is applied/formed from an organic semiconductor solution, in a single solvent system, excessive aggregation of the electron accepting organic semiconductor or the like easily occurs in the process in which the organic semiconductor composition is dried/condensed after applying a solution because of insufficient affinity of the solvent for the electron accepting organic semiconductor. Therefore, a phase-separation size of the photoelectric conversion layer becomes excessively larger than 20 nm (as the phase-separation size, about 20 nm which is about two times as large as an exciton diffusion distance of an organic semiconductor (generally, about 10 nm) is thought to be suitable) and it has been difficult to adjust the photoelectric conversion layer to an appropriate size. Further, a solvent having high affinity for the electron accepting organic semiconductor, is excessively high in a boiling point and it has been difficult to apply the photoelectric conversion layer in an appropriate thickness in such a single solvent system.

A method of solving those problems includes a method of combining a solvent with an additive. As disclosed in the above-mentioned ("Advanced Materials," vol. 22, p. E135-E138, 2010, it is reported that by adding a specific additive (1,8-diiodooctane) to a solution of forming a photoelectric conversion layer, a structure of phase-separation (phase-separation size, co-continuity, orientation) between the electron donating organic semiconductor and the electron accepting organic semiconductor varies to improve photoelectric conversion efficiency.

Moreover, when an additive can achieve the effect of improving performance even in small amounts, it is easy to obtain a cost advantage by combining the additive with a low-cost solvent. Further, since viscosity and drying property of a solution can be determined, it is easy to adjust characteristics of a composition according to an application method to be used. Further, even when a solvent is a high boiling point compound which is difficult to dry or such a compound that is solid at ordinary temperatures and pressures, a process advantage that drying becomes easy or it becomes possible to apply as a solution by adding a small amount of additive, is possible.

We confirmed that when the 1,8-diiodooctane is added as an additive in applying/forming a photoelectric conversion layer composed of the electron donating organic semiconductor and the electron accepting organic semiconductor, the photoelectric conversion efficiency is improved certainly. However, we believe that 1,8-diiodooctane has a high boiling point and low volatility resulting in slow drying, and thereby deterioration of processing properties and concerns about durability due to instability of a halogen compound become problems. Furthermore, we also believe that since 1,8-diiodooctane is a halogen compound, a non-halogen compound is preferred as an alternative to 1,8-diiodooctane also from the viewpoint of environmental load.

It could therefore be helpful to provide an organic semiconductor composition that can achieve high photoelectric conversion efficiency equal to the case of using 1,8-diiodooctane as an additive, and has good processing properties and low environmental load, and a photovoltaic element using the organic semiconductor composition.

SUMMARY

We provide an organic semiconductor composition including an electron donating organic semiconductor, an electron accepting organic semiconductor, a solvent and an additive having a boiling point higher than that of the solvent, wherein the additive is one or two or more compounds selected from the group consisting of compounds represented by any one of formulae (1) to (3):

 (1)

 (2)

 (3)

in which in formula (1), A represents any aromatic hydrocarbon group having one ring or a heteroaromatic group having one ring, n is a natural number of 2 or more, $R_1$s are n of substituents coupled with the A at an arbitrary position, may be the same or different, and represent an alkyl group, an alkoxy group or an alkanoyl group, further, at least one among a plurality of $R_1$s is either an alkoxy group or an alkanoyl group, plurality of $R_1$s may be combined with one another to form a ring; in which in formula (2), B represents any aromatic hydrocarbon group having two rings or a heteroaromatic group having two rings, n is a natural number of 1 or more, $R_2$s are n of substituents coupled with the B at an arbitrary position, may be the same or different, and represent an alkyl group, an alkoxy group, an alkanoyl group or a thioalkyl group, further, at least one among $R_2$s is any one of an alkoxy group, an alkanoyl group and a thioalkyl group, a plurality of $R_2$s may be combined with one another to form a ring; and in which in formula (3), C represents any aromatic hydrocarbon group having one ring or a heteroaromatic group having one ring, n is a natural number of 1 or more, $R_3$s are n of substituents coupled with the C at an arbitrary position, may be the same or different, and represent an alkyl group, an alkoxy group, an alkanoyl group or a thioalkyl group, further, at least one among $R_3$s is a thioalkyl group a plurality of $R_3$s may be combined with one another to form a ring.

We also provide the organic semiconductor composition including an electron donating organic semiconductor, an electron accepting organic semiconductor, a solvent and an additive having a boiling point higher than that of the solvent, wherein the additive is one or two or more compounds selected from the group consisting of compounds represented by any one of formulae (1) to (3):

 (1)

 (2)

 (3)

in which in formula (1), A represents any aromatic hydrocarbon group having one ring or a heteroaromatic group having one ring, n is a natural number of 2 or more, $R_1$s are n of substituents coupled with the A at an arbitrary position, may be the same or different, and represent an alkyl group, an alkoxy group or an alkanoyl group, further, at least one among a plurality of $R_1$s is either an alkoxy group or an alkanoyl group, plurality of $R_1$s may be combined with one another to form a ring; in which in formula (2), B represents any aromatic hydrocarbon group having two rings or a heteroaromatic group having two rings, n is a natural number of 1 or more, $R_2$s are n of substituents coupled with the B at an arbitrary position, may be the same or different, and represent an alkyl group, an alkoxy group, an alkanoyl group or a thioalkyl group, further, at least one among $R_2$s is any one of an alkoxy group, an alkanoyl group and a thioalkyl group, a plurality of $R_2$s may be combined with one another to form a ring; and in which in formula (3), C represents any aromatic hydrocarbon group having one ring or a heteroaromatic group having one ring, n is a natural number of 1 or more, $R_3$s are n of substituents coupled with the C at an arbitrary position, may be the same or different, and represent an alkyl group, an alkoxy group, an alkanoyl group or a thioalkyl group, further, at least one among $R_3$s is a thioalkyl group a plurality of $R_3$s may be combined with one another to form a ring, wherein the electron donating organic semiconductor includes a conjugated polymer having a skeleton represented by any one of formulae (4) to (6):

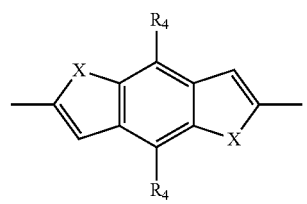 (4)

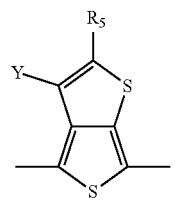 (5)

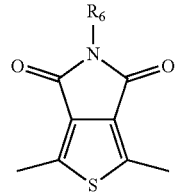 (6)

in which in formula (4), $R_4$s which may be the same or different represent an alkyl group, an alkoxy group, an optionally substituted heteroaryl group, an optionally substituted aryl group or a thioalkoxy group, and X which may be the same or different represents a sulfur atom, a selenium atom or an oxygen atom; in which in formula (5), $R_5$s represent an alkoxycarbonyl group or an alkanoyl group, and Y represents a hydrogen atom or a halogen atom; and in which in formula (6), $R_6$s represent an alkyl group, an optionally substituted heteroaryl group or an optionally substituted aryl group.

We further provide the organic semiconductor composition including an electron donating organic semiconductor, an electron accepting organic semiconductor, a solvent and an additive having a boiling point higher than that of the solvent, wherein the additive is one or two or more compounds selected from the group consisting of compounds represented by any one of formulae (1) to (3):

 (1)

 (2)

 (3)

in which in formula (1), A represents any aromatic hydrocarbon group having one ring or a heteroaromatic group having one ring, n is a natural number of 2 or more, $R_1$s are n of substituents coupled with the A at an arbitrary position, may be the same or different, and represent an alkyl group, an alkoxy group or an alkanoyl group, further, at least one among a plurality of $R_1$s is either an alkoxy group or an alkanoyl group, plurality of $R_1$s may be combined with one another to form a ring; in which in formula (2), B represents any aromatic hydrocarbon group having two rings or a heteroaromatic group having two rings, n is a natural number of 1 or more, $R_2$s are n of substituents coupled with the B at an arbitrary position, may be the same or different, and represent an alkyl group, an alkoxy group, an alkanoyl group or a thioalkyl group, further, at least one among $R_2$s is any one of an alkoxy group, an alkanoyl group and a thioalkyl group, a plurality of $R_2$s may be combined with one another to form a ring; and in which in formula (3), C represents any aromatic hydrocarbon group having one ring or a heteroaromatic group having one ring, n is a natural number of 1 or more, $R_3$s are n of substituents coupled with the C at an arbitrary position, may be the same or different, and represent an alkyl group, an alkoxy group, an alkanoyl group or a thioalkyl group, further, at least one among $R_3$s is a thioalkyl group a plurality of $R_3$s may be combined with one another to form a ring, wherein the electron donating organic semiconductor includes a conjugated polymer having a skeleton represented by any one of formulae (4) to (6):

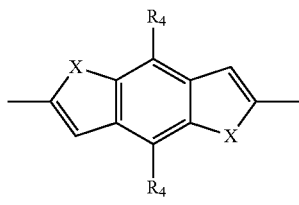
(4)

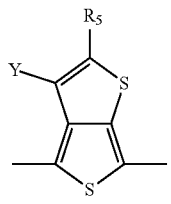
(5)

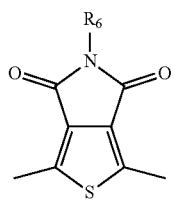
(6)

in which in formula (4), $R_4$s which may be the same or different represent an alkyl group, an alkoxy group, an optionally substituted heteroaryl group, an optionally substituted aryl group or a thioalkoxy group, and X which may be the same or different represents a sulfur atom, a selenium atom or an oxygen atom; in which in formula (5), $R_5$s represent an alkoxycarbonyl group or an alkanoyl group, and Y represents a hydrogen atom or a halogen atom; and in which in formula (6), $R_6$s represent an alkyl group, an optionally substituted heteroaryl group or an optionally substituted aryl group, wherein the conjugated polymer is a conjugated polymer represented by formula (7):

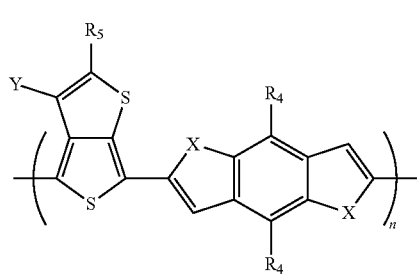
(7)

in which $R_4$s which may be the same or different represent an alkyl group, an alkoxy group, an optionally substituted heteroaryl group, an optionally substituted aryl group or a thioalkoxy group, $R_5$s represent an alkoxycarbonyl group or an alkanoyl group, X which may be the same or different represents a sulfur atom, a selenium atom or an oxygen atom, and Y represents a hydrogen atom or a halogen atom.

We also provide a photovoltaic element having an anode, a cathode and a photoelectric conversion layer formed by drying the organic semiconductor composition including an electron donating organic semiconductor, an electron accepting organic semiconductor, a solvent and an additive having a boiling point higher than that of the solvent, wherein the additive is one or two or more compounds selected from the group consisting of compounds represented by any one of formulae (1) to (3):

$$A\text{---}[R_1]_n \quad (1)$$

$$B\text{---}[R_2]_n \quad (2)$$

$$C\text{---}[R_3]_n \quad (3)$$

in which in formula (1), A represents any aromatic hydrocarbon group having one ring or a heteroaromatic group having one ring, n is a natural number of 2 or more, $R_1$s are n of substituents coupled with the A at an arbitrary position, may be the same or different, and represent an alkyl group, an alkoxy group or an alkanoyl group, further, at least one among a plurality of $R_1$s is either an alkoxy group or an alkanoyl group, plurality of $R_1$s may be combined with one another to form a ring; in which in formula (2), B represents any aromatic hydrocarbon group having two rings or a heteroaromatic group having two rings, n is a natural number of 1 or more, $R_2$s are n of substituents coupled with the B at an arbitrary position, may be the same or different, and represent an alkyl group, an alkoxy group, an alkanoyl group or a thioalkyl group, further, at least one among $R_2$s is any one of an alkoxy group, an alkanoyl group and a thioalkyl group, a plurality of $R_2$s may be combined with one another to form a ring; and in which in formula (3), C represents any aromatic hydrocarbon group having one ring or a heteroaromatic group having one ring, n is a natural number of 1 or more, $R_3$s are n of substituents coupled with the C at an arbitrary position, may be the same or different, and represent an alkyl group, an alkoxy group, an alkanoyl group or a thioalkyl group, further, at least one among $R_3$s is a thioalkyl group a plurality of $R_3$s may be combined with one another to form a ring, which is formed between the anode and the cathode.

We also provide a method of manufacturing a photovoltaic element having an anode, a cathode and a photoelectric conversion layer formed between the anode and the cathode, wherein the photoelectric conversion layer is formed by applying/drying the organic semiconductor composition including an electron donating organic semiconductor, an electron accepting organic semiconductor, a solvent and an additive having a boiling point higher than that of the solvent, wherein the additive is one or two or more compounds selected from the group consisting of compounds represented by any one of formulae (1) to (3):

(1)

(2)

(3)

in which in formula (1), A represents any aromatic hydrocarbon group having one ring or a heteroaromatic group having one ring, n is a natural number of 2 or more, $R_1$s are n of substituents coupled with the A at an arbitrary position, may be the same or different, and represent an alkyl group, an alkoxy group or an alkanoyl group, further, at least one among a plurality of $R_1$s is either an alkoxy group or an alkanoyl group, plurality of $R_1$s may be combined with one another to form a ring; in which in formula (2), B represents any aromatic hydrocarbon group having two rings or a heteroaromatic group having two rings, n is a natural number of 1 or more, $R_2$s are n of substituents coupled with the B at an arbitrary position, may be the same or different, and represent an alkyl group, an alkoxy group, an alkanoyl group or a thioalkyl group, further, at least one among $R_2$s is any one of an alkoxy group, an alkanoyl group and a thioalkyl group, a plurality of $R_2$s may be combined with one another to form a ring; and in which in formula (3), C represents any aromatic hydrocarbon group having one ring or a heteroaromatic group having one ring, n is a natural number of 1 or more, $R_3$s are n of substituents coupled with the C at an arbitrary position, may be the same or different, and represent an alkyl group, an alkoxy group, an alkanoyl group or a thioalkyl group, further, at least one among $R_3$s is a thioalkyl group a plurality of $R_3$s may be combined with one another to form a ring.

It is possible to provide a photovoltaic element having high photoelectric conversion efficiency as well as excellent processing properties/low environmental load by forming a photoelectric conversion layer from the composition.

BRIEF DESCRIPTION OF THE DRAWING

FIG. 1 is a sectional view showing an aspect of our photovoltaic element.

DESCRIPTION OF REFERENCE SIGNS

1: Substrate
2: Anode
3: Hole extraction layer
4: Photoelectric conversion layer
5: Electron extraction layer
6: Cathode

DETAILED DESCRIPTION

We found that the affinity for the electron accepting organic semiconductor of 1,8-diiodooctane is high, and believed that the high affinity is a factor in controlling the structure. Further, we found that the high affinity for the electron accepting organic semiconductor of 1,8-diiodooctane is derived from a halogen atom. Accordingly, to change the 1,8-diiodooctane to non-halogen compound, an entirely different skeleton or substituent having high affinity for the electron accepting organic semiconductor is required. We further found that an aromatic ring such as benzene is effective for a skeleton having the high affinity for the electron accepting organic semiconductor, and an alkoxy group, an alkanoyl group or a thioalkyl group is effective for a substituent having the high affinity for the electron accepting organic semiconductor. That is, an organic semiconductor composition includes an electron donating organic semiconductor, an electron accepting organic semiconductor, a solvent and an additive having a boiling point higher than that of the solvent, wherein the additive is one or two or more compounds selected from the group consisting of compounds represented by any one of formulae 1 to 3 described below.

Organic Semiconductor Composition

Our organic semiconductor composition will be described.

Our organic semiconductor composition includes an electron donating organic semiconductor, an electron accepting organic semiconductor, a solvent and an additive a boiling point of which is higher than that of the solvent, wherein the additive is one or two or more compounds selected from the group consisting of compounds represented by any one of formulae 1 to 3 described below.

Electron Donating Organic Semiconductor

The electron donating organic semiconductor is an organic compound exhibiting p-type semiconductor properties or having hole transporting properties, and it is not particularly limited as long as it is a compound having these properties. Examples of the organic compound exhibiting p-type semiconductor properties or having hole transporting properties include conjugated polymers such as a polythiophene polymer, a 2,1,3-benzothiadiazole-thiophene copolymer, a quinoxaline-thiophene copolymer, a thienothiophene-benzodithiophene copolymer, a thienopyrroledione copolymer, an isoindigo copolymer, a diketopyrrolopyrrole copolymer, a poly(p-phenylenevinylene) polymer, a poly(p-phenylene) polymer, a polyfluorene polymer, a polypyrrole polymer, a polyaniline polymer, a polyacetylene polymer, and a poly(thienylene vinylene) polymer; and low-molecular weight organic compounds including phthalocyanine derivatives such as $H_2$ phthalocyanine ($H_2$Pc), copper phthalocyanine (CuPc) and zinc phthalocyanine (ZnPc), porphyrin derivatives, triaryl amine derivatives such as porphyrin derivatives, N,N'-diphenyl-N,N'-di(3-methylphenyl)-4,4'-diphenyl-1,1'-diamine (TPD) and N,N'-dinaphthyl-N,N'-diphenyl-4,4'-diphenyl-1,1'-diamine (NPD), carbazole derivatives such as 4,4'-di(carbazole-9-yl)biphenyl (CBP), and oligothiophene derivatives (terthiophene, quaterthiophene, sexithiophene, octithiophene and the like). Two or more thereof may be mixed for use.

The polythiophene polymer refers to a conjugated polymer having a thiophene skeleton in a main chain, and also includes a conjugated polymer having a side chain. Specific examples thereof include poly(3-alkylthiophene) such as poly(3-methylthiophene), poly(3-butylthiophene), poly(3-hexylthiophene), poly(3-octylthiophene) and poly(3-decylthiophene); poly(3-alkoxythiophene) such as poly(3-methoxylthiophene), poly(3-ethoxylthiophene) and poly(3-dodecyloxyl)thiophene; and poly(3-alkoxy-4- alkylthiophene) such as poly(3-methoxy-4-methylthiophene) and poly(3-dodecyloxy-4-methylthiophene).

The 2,1,3-benzothiadiazole-thiophene copolymer refers to a conjugated copolymer having a thiophene skeleton and a 2,1,3-benzothiadiazole skeleton in a main chain. Specific examples of the 2,1,3-benzothiadiazole-thiophene copolymer include copolymers having the following structures. In the following formula, n represents an integer of 1 to 1000:

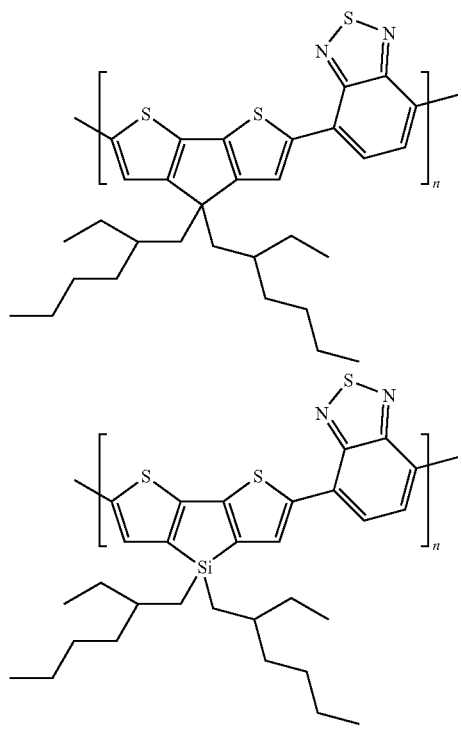

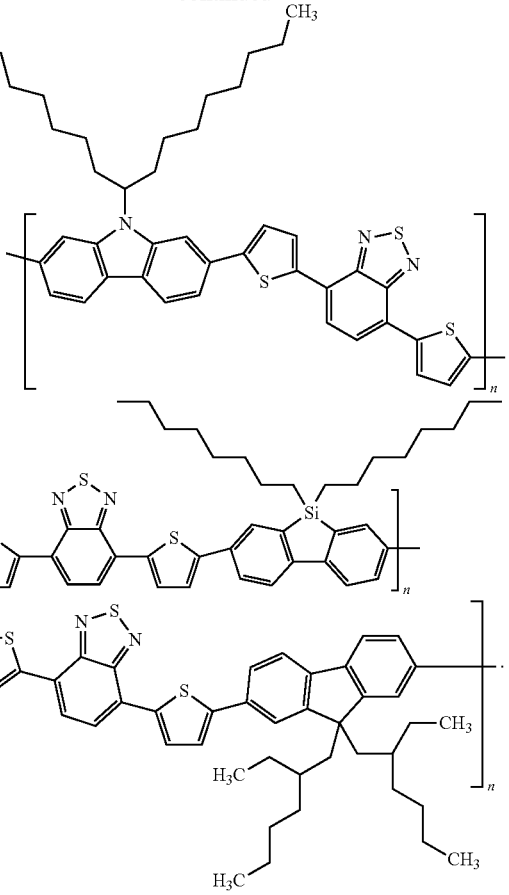

The quinoxaline-thiophene copolymer refers to a conjugated copolymer having a thiophene skeleton and a quinoxaline skeleton in a main chain. Specific examples of the quinoxaline-thiophene copolymer include copolymers having the following structures. In the following formula, n represents an integer of 1 to 1000:

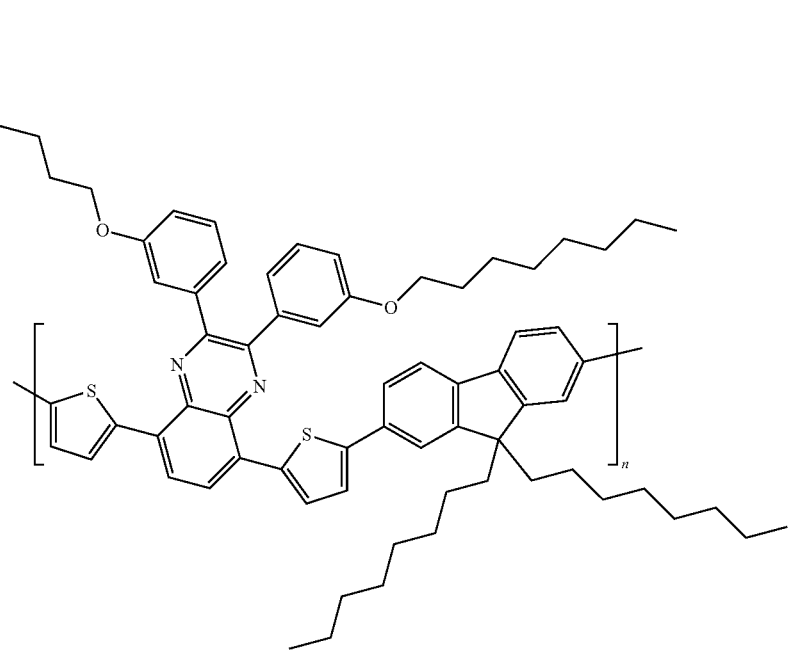

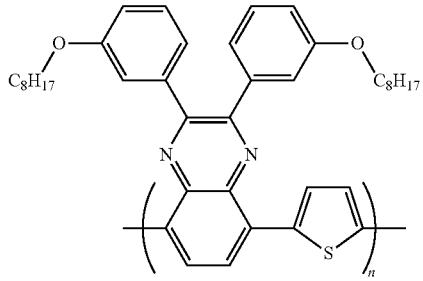
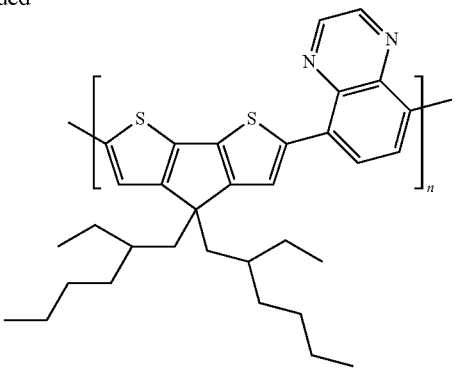
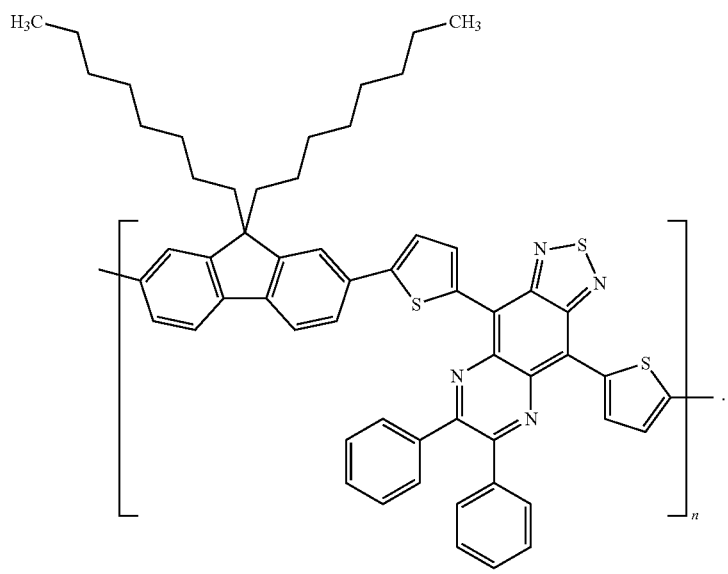
The thienothiophene-benzothiophene copolymer refers to a conjugated copolymer having a thiophene skeleton and a benzothiophene skeleton in a main chain. Specific examples of the thiophene-benzothiophene copolymer include copolymers having the following structures. In the following formula, n represents an integer of 1 to 1000:
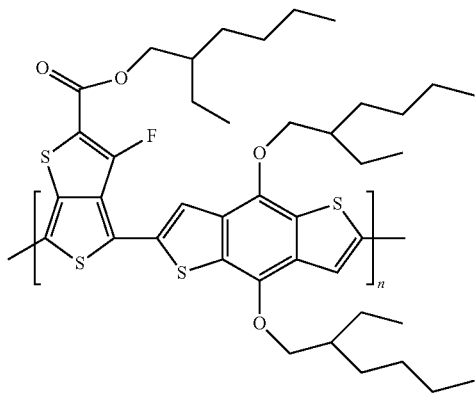
-continued
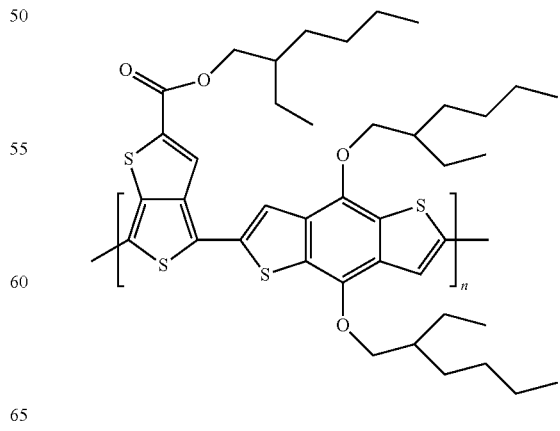

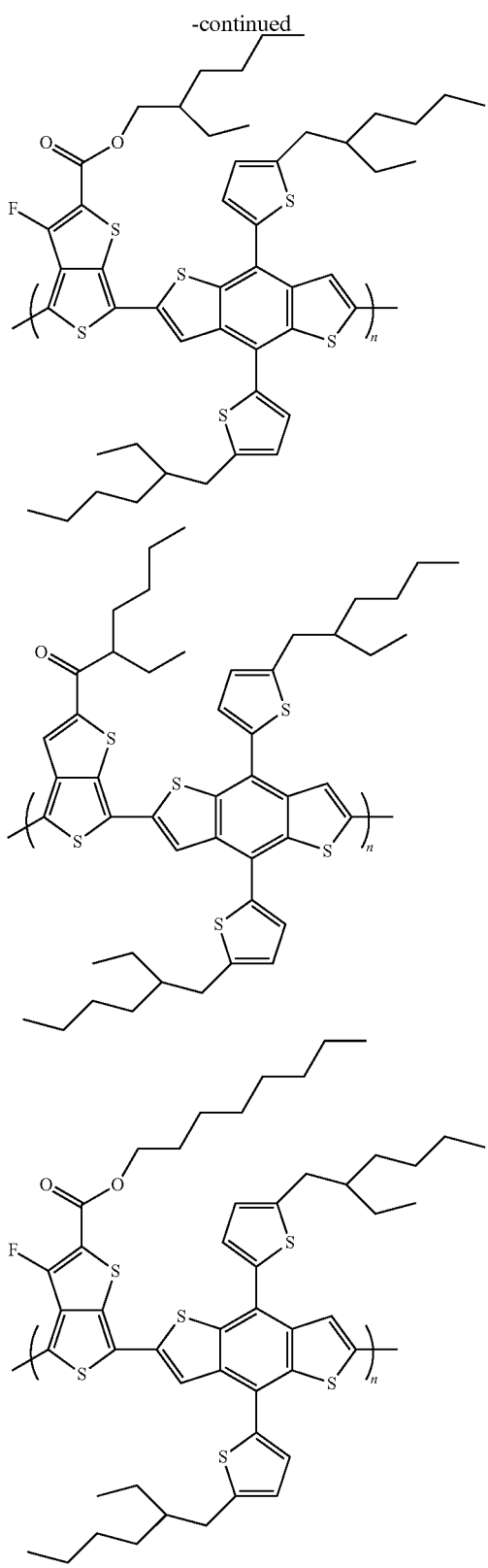
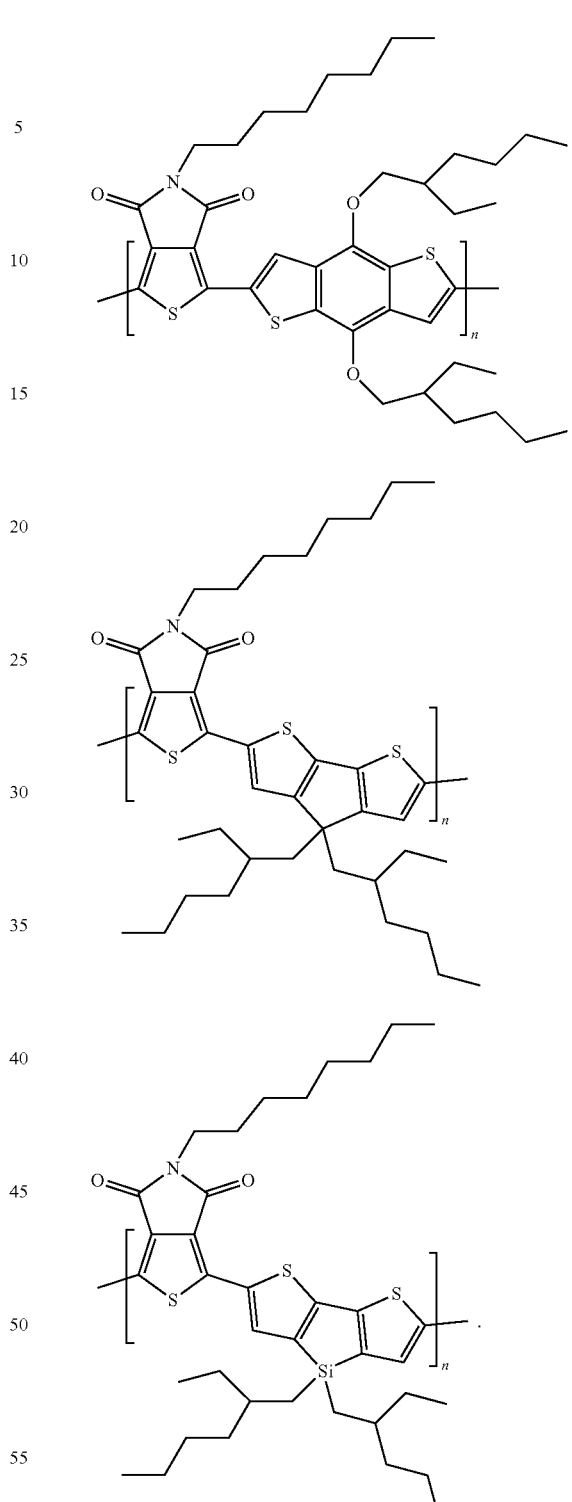

The thienopyrroledione copolymer refers to a conjugated copolymer having a thienopyrroledione skeleton in a main chain. Specific examples of the thienopyrroledione copolymer include copolymers having the following structures. In the following formula, n represents an integer of 1 to 1000:

The poly(p-phenylenevinylene) polymer refers to a conjugated polymer having a polyphenylenevinylene skeleton in a main chain and also includes a conjugated polymer having a side chain. Specific examples thereof include poly[2-methoxy-5-(2-ethylhexyloxy)-1,4-phenylenevinylene], poly[2-methoxy-5-(3',7'-dimethyloctyloxy)-1,4-phenylenevinylene] and the like.

It is reported in large numbers that in a conjugated polymer having a skeleton represented by any one of the following formulae (4) to (6) among the electron donating organic semiconductor as exemplified above, photovoltaic characteristics are improved when using 1,8-diiodooctane as an additive (e.g., patent no. 05829734 specification, "Advanced Materials," vol. 22, p. E135-E138, 2010, "Journal of the American Chemistry, vol. 132, p. 7595-7597, 2010," "Macromolecules, vol. 45, p. 6923-6929, 2012," "Advanced Materials," vol. 23, p. 3315-3319, 2011), and it is preferred to contain a conjugated polymer having a skeleton represented by any one of formulae (4) to (6) as the electron donating organic semiconductor of the composition.

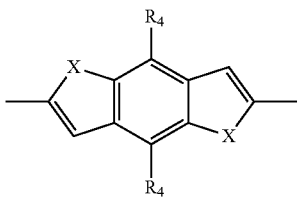

(4)

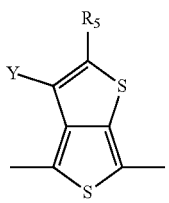

(5)

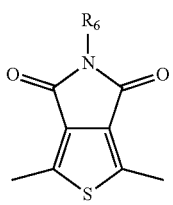

(6)

In formula (4), $R_4$s which may be the same or different represent an alkyl group, an alkoxy group, an optionally substituted heteroaryl group, an optionally substituted aryl group or a thioalkoxy group. X which may be the same or different represents a sulfur atom, a selenium atom or an oxygen atom.

In formula (5), $R_5$s represent an alkoxycarbonyl group or an alkanoyl group. Y represents a hydrogen atom or a halogen atom.

In formula (6), $R_6$s represent an alkyl group, an optionally substituted heteroaryl group or an optionally substituted aryl group.

Among the conjugated polymers having the above skeleton structure, a conjugated polymer represented by formula (7) is more preferred as the electron donating organic semiconductor of the composition since it has a wide optical absorption wavelength region and a deep HOMO level and therefore it can achieve high photovoltaic characteristics.

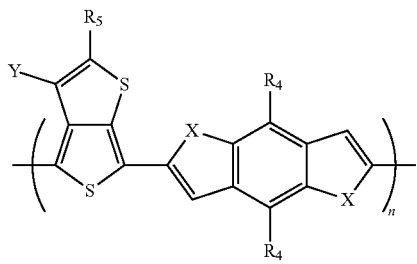

(7)

In formula (7), $R_4$, $R_5$, X and Y are similar to those of formulae (4) and (5). Electron Accepting Organic Semiconductor The electron accepting organic semiconductor is an organic compound exhibiting n-type semiconductor properties or having electron transporting properties, and it is not particularly limited as long as it is a compound having these properties. Examples of the organic compound exhibiting n-type semiconductor properties or having electron transporting properties include 1,4,5,8-naphthalene tetracarboxylic dianhydride, N,N'-dioctyl-3,4,9,10-naphthyltetracarboxy diimide, perylene derivatives (3,4,9,10-perylenetetracarboxylic dianhydride, perylene diimide derivatives, perylene diimide dimer, perylene diimide polymer and the like), oxazole derivatives (2-(4-biphenylyl)-5-(4-t-butylphenyl)-1,3,4-oxadiazole), 2,5-di(1-naphthyl)-1,3, 4-oxadiazole and the like), triazole derivatives (3-(4-biphenylyl)-4-phenyl-5-(4-t-butylphenyl)-1,2,4-triazole and the like), phenanthroline derivatives, fullerene derivatives, carbon nano-tubes, and a derivative (CN-PPV) prepared by introducing a cyano group to a poly(p-phenylenevinylene) polymer. Two or more thereof may be mixed for use. Among these organic compounds, fullerene derivatives are preferably used since they are n-type semiconductors which is stable and high in carrier mobility.

Specific examples of the fullerene derivatives include: unsubstituted fullerene derivatives including $C_{60}$, $C_{70}$, $C_{76}$, $C_{78}$, $C_{82}$, $C_{84}$, $C_{90}$ and $C_{94}$; and substituted fullerene derivatives including [6,6]-phenyl C61 butyric acid methylester ([6,6]-C61-PCBM, or [60]PCBM), [5,6]-phenyl C61 butyric acid methylester, [6,6]-phenyl C61 butyric acid hexylester, [6,6]-phenyl C61 butyric acid dodecylester, and phenyl C71 butyric acid methylester ([70]PCBM). Among these, [70] PCBM is more preferred since it has a wide optical absorption wavelength region.

The contents of the electron donating organic semiconductor and the electron accepting organic semiconductor is not particularly limited as long as they can be both dissolved or dispersed in the composition. However, the ratio by weight between the electron donating organic semiconductor and the electron accepting organic semiconductor is preferably 1 to 99:99 to 1, more preferably 20 to 80:80 to 20. However, in any weight ratio, a sum of weights of the electron donating organic semiconductor component and the electron accepting organic semiconductor component is preferably 0.1 to 10 wt %, and more preferably 1.0 to 5.0 wt % with respect to a total of a solvent and an additive described later.

Solvent

The solvent is not particularly limited as long as it is a solvent in which the electron donating organic semiconductor and electron accepting organic semiconductor are dissolved or dispersed to form a uniform solution. Accordingly, an appropriate solvent varies with the solubility of the electron donating organic semiconductor and the electron accepting organic semiconductor, and examples thereof include water; aliphatic hydrocarbons such as hexane, heptane, octane, isooctane, nonane, decane, cyclohexane, decalin and bicyclohexyl; alcohols such as methanol, ethanol, butanol, propanol, ethylene glycol and glycerin; ketones such as acetone, methyl ethyl ketone, cyclopentanone, cyclohexanone and isophorone; esters such as ethyl acetate, butyl acetate, methyl lactate, γ-butyrolactone, diethylene glycol monobutyl ether acetate and dimethyl carbonate; ethers such as ethyl ether, methyl tert-butyl ether, tetrahydrofuran, 1,4-dioxane, tetrahydropyran, 3,4-dihydro-2H-pyran, isochroman, ethylene glycol monomethyl ether and diglyme; amines such as ammonia and ethanol amine; amides such as N,N-dimethylformamide, dimethylacetamide and N-methyl-2-pyrrolidone; sulfones such as sulfolane; sulfoxides such as dimethyl sulfoxide; carbon disulfide; thiols such as 1,8-octanedithiol; nitriles such as acetonitrile and acrylonitrile; fatty acids such as acetic acid and lactic acid; heterocyclic compounds such as furan, thiophene, pyrrole and pyridine; aromatic hydrocarbons such as benzene, toluene, xylene, ethylbenzene, cumene, n-butylbenzene, sec-butylbenzene, tert-butylbenzene, styrene, mesitylene, 1,2,4-trimethylbenzene, p-cymene, cyclohexylbenzene, diethylbenzene, pentylbenzene, dipentylbenzene, dodecylbenzene, ethynylbenzene, tetralin, anisole, phenetol, butyl phenyl ether, pentyl phenyl ether, 1,2-dimethoxybenzene, 1,3-dimethoxybenzene, 1,2,4-trimethoxybenzene, 2-methoxytoluene, 2,5-dimethylanisole, o-chlorophenol, chlorobenzene, dichlorobenzene, trichlorobenzene, 1-chloronaphthalene, 1-bromonaphthalene, 1-methylnaphthalene, o-diiodobenzene, acetophenone, 2,3-benzofuran, 2,3-dihydrobenzofuran, 1,4-benzodioxane, phenyl acetate, methyl benzoate, cresol, aniline and nitrobenzene; and halogen hydrocarbons such as dichloromethane, 1,2-dichloroethylene, trichloroethylene, tetrachloroethylene, chloroform, carbon tetrachloride, dichloroethane, trichloroethane, 1,3-dichloropropane, 1,1,1,2-tetrachloroethane, 1,1,1,3-tetrachloropropane, 1,2,2,3-tetrachloropropane, 1,1,2,3-tetrachloropropane, pentachloropropane, hexachloropropane, heptachloropropane, 1-bromopropane, 1,2-dibromopropane, 2,2-dibromopropane, 1,3-dibromopropane, 1,2,3-tribromopropane, 1,4-dibromobutane, 1,5-dibromopentane, 1,6-dibromohexane, 1,7-dibromoheptane, 1,8-dibromooctane, 1-iodopropane, 1,3-diiodopropane, 1,4-diiodobutane, 1,5-diiodopentane, 1,6-diiodohexane, 1,7-diiodoheptane and 1,8-diiodooctane.

Among these solvents, aromatic hydrocarbons such as toluene, xylene, mesitylene, 1,2,4-trimethylbenzene, tetralin, anisole, phenetol, veratrole, 1,3-dimethoxybenzene, 1,2,4-trimethoxybenzene, 2-methoxytoluene, 2,5-dimethylanisole, chlorobenzene, dichlorobenzene, trichlorobenzene and 1-chloronaphthalene; and halogen hydrocarbons such as chloroform and dichloromethane can be preferably used when dissolving organic semiconductor component which is typically a conjugated compound. Moreover, from the viewpoint of environmental load, toluene, xylene, mesitylene, 1,2,4-trimethylbenzene, tetralin, anisole, phenetol, 1,2-dimethoxybenzene, 1,3-dimethoxybenzene, 1,2,4-trimethoxybenzene, 2-methoxytoluene, 2,5-dimethylanisole and the like, which are non-halogen solvents, are more preferably used. In addition, two or more thereof may be mixed for use separately from specific additive described later.

Additive

The additive contained in the organic semiconductor composition is one or two or more compounds selected from the group consisting of compounds represented by any one of formulae (1) to (3):

(1)

(2)

(3)

in which in formula (1), A represents any aromatic hydrocarbon group having one ring or a heteroaromatic group having one ring, n is a natural number of 2 or more, $R_1$s are n of substituents coupled with the A at an arbitrary position, may be the same or different, and represent an alkyl group, an alkoxy group or an alkanoyl group, at least one among a plurality of $R_1$s is either an alkoxy group or an alkanoyl group, and a plurality of $R_1$s may be combined with one another to form a ring, in which in formula (2), B represents any aromatic hydrocarbon group having two rings or a heteroaromatic group having two rings, n is a natural number of 1 or more, $R_2$s are n of substituents coupled with the B at an arbitrary position, may be the same or different, and represent an alkyl group, an alkoxy group, an alkanoyl group or a thioalkyl group, at least one among $R_2$s is any one of an alkoxy group, an alkanoyl group and a thioalkyl group, and a plurality of $R_2$s may be combined with one another to form a ring, and in which in formula (3), C represents any aromatic hydrocarbon group having one ring or a heteroaromatic group having one ring, n is a natural number of 1 or more, $R_3$s are n of substituents coupled with the C at an arbitrary position, may be the same or different, and represent an alkyl group, an alkoxy group, an alkanoyl group or a thioalkyl group, at least one among $R_3$s is a thioalkyl group, and a plurality of $R_3$s may be combined with one another to form a ring.

In formula (1), the A is any aromatic hydrocarbon group having one ring or a heteroaromatic group having one ring, and examples thereof include a benzene ring, a thiophene ring, a pyridine ring, a pyrimidine ring, a pyridazine ring, a pyrazine ring, a triazine ring, a furan ring, a pyrrole ring, an imidazole ring, a pyrazole ring, an oxazole ring, an isoxazole ring, a thiazole ring, an isothiazole ring, and the like. Since the A is an aromatic hydrocarbon group having one ring or a heteroaromatic group having one ring, the affinity for the electron accepting organic semiconductor which is often a conjugated material, is enhanced. Among these ring structures, a benzene ring is preferred as A from the viewpoint of stability, versatility and easy handleability.

In formula (1), $R_1$s are n of substituents coupled with the A at an arbitrary position, may be the same or different, and represent an alkyl group, an alkoxy group or an alkanoyl group.

Herein, the alkyl group refers to a saturated aliphatic hydrocarbon group such as a methyl group, an ethyl group, a propyl group and a butyl group and may be linear or branched. Alkoxy group represents hydrocarbon groups with an ether bond interposed therebetween such as a methoxy group, an ethoxy group, a propoxy group and a butoxy group, and the hydrocarbon group may be linear or branched. Alkanoyl group represents alkyl groups with a ketone group interposed therebetween or alkoxy groups with a ketone group interposed therebetween, and the alkyl group and the alkoxy group may be linear or branched. Further, in the case of not forming a ring, the alkyl group is preferably shorter in a length so that a density at a site having high affinity for the electron accepting organic semiconductor is not decreased, and therefore the alkyl group is preferably a methyl group.

Further, a plurality of R1s may be combined with one another to form a ring and, for example, an alkoxy group may be combined with an alkyl group to form a dihydrofuran ring or a dihydropyran ring, an alkoxy group may be combined with an alkoxy group to form a 1,4-dioxane ring, or an alkanoyl group may be combined with an alkyl group to form a cyclohexanone ring or a cyclopentanone ring. Formation of a ring is one of preferred additive structures since by formation of a ring, the affinity for the electron accepting organic semiconductor which is often a conjugated material, may be enhanced.

Further, at least one among a plurality of $R_1$s is either an alkoxy group or an alkanoyl group. By having one or more of these substituents, the affinity of the additive for the electron accepting organic semiconductor is enhanced and dispersibility of the electron accepting organic semiconductor is improved. From the viewpoint of the affinity for the electron accepting organic semiconductor, it is preferred that two or more $R_1$s of a plurality of $R_1$s are an alkoxy group, or two or more $R_1$s are an alkanoyl group and an alkyl group and form a ring. Moreover, it is more preferred that n is 3 or more and three or more $R_1$s are an alkoxy group. Further, the alkoxy group is preferably shorter in a length so that a density at a site having high affinity for the electron accepting organic semiconductor is not decreased and, therefore, the alkoxy group is preferably a methoxy group.

Specific examples of the compounds represented by formula (1) include benzene compounds substituted with one or more alkoxy groups and alkyl groups such as 2-methoxytoluene, 3-methoxytoluene, 4-methoxytoluene and 2,5-dimethylanisole; benzene compounds such as 2,3-dihydrobenzofuran, 1,4-benzodioxane, a-tetralone and 1-indanone, in which a substituent such as an alkoxy group, an alkanoyl group or an alkyl group forms a ring; dimethoxybenzene position isomers such as 1,2-dimethoxybenzene, 1,3-dimethoxybenzene and 1,4-dimethoxybenzene; dimethoxytoluene position isomers such as 3,5-dimethoxytoluene, 3,4-dimethoxytoluene, 2,4-dimethoxytoluene and 2,5-dimethoxytoluene; trimethoxybenzene position isomers such as 1,2,3-trimethoxybenzene, 1,2,4-trimethoxybenzene and 1,3,5-trimethoxybenzene; trimethoxytoluene position isomers such as 3,4,5-trimethoxytoluene and 2,4,6-trimethoxytoluene; tetramethoxybenzene position isomers such as 1,2,4,5-tetramethoxybenzene, 1,2,3,5-tetramethoxybenzene and 1,2,3,4-tetramethoxybenzene; and tetramethoxybenzene position isomers such as 2,3,4,5-tetramethoxytoluene. However, these compounds are examples, and the compound represented by formula (1) is not limited to these compounds.

In formula (2), the B is any aromatic hydrocarbon group having two rings or a heteroaromatic group having two rings, and examples thereof include a naphthalene ring, an indene ring, a benzofuran ring, an indole ring, a benzimidazole ring, a purine ring, a quinoline ring, an isoquinoline ring, a quinazoline ring, a phthalazine ring, a pteridin ring, a coumarin ring, a chromone ring, and the like. Among these, the naphthalene ring is preferred from the viewpoint of stability, versatility and easy handleability.

$R_2$s are n of substituents coupled with the B at an arbitrary position, may be the same or different, and represent an alkyl group, an alkoxy group, an alkanoyl group or a thioalkyl group. The alkyl group, the alkoxy group and the alkanoyl group are similar to those in the above-mentioned $R_1$. Thioalkyl group represents alkyl groups with a thioether bond interposed therebetween, and the alkyl group may be linear or branched. In addition, the reason why number of substitutions (n) of the B of 1 or more is sufficient in the compound of formula (2) and the number of substitutions is allowed to be smaller than the number of substitutions (2 or more) of the A in the compound of formula (1) is supposedly that since the B has two rings, it has the affinity for the electron accepting organic semiconductor higher than the A having one ring.

Further, at least one among $R_2$s is any one of an alkoxy group, an alkanoyl group and a thioalkyl group. By having one or more of these substituents, the affinity of the additive for the electron accepting organic semiconductor is enhanced and dispersibility of the electron accepting organic semiconductor is improved. A plurality of $R_2$s may be combined with one another to form a ring. Formation of a ring is similar to the above-mentioned $R_1$.

Specific examples of the compounds represented by formula (2) include methoxynaphthalene position isomers such as 1-methoxynaphthalene and 2-methoxynaphthalene; dimethoxynaphthalene position isomers such as 1,4-dimethoxynaphthalene, 1,6-dimethoxynaphthalene, 1,7-dimethoxynaphthalene, 2,3-dimethoxynaphthalene, 2,6-dimethoxynaphthalene and 2,7-dimethoxynaphthalene; and methoxybenzofuran position isomers such as 7-methoxybenzofuran. However, these compounds are examples, and the compound represented by formula (2) is not limited to these compounds.

In formula (3), the C is any aromatic hydrocarbon group having one ring or a heteroaromatic group having one ring, and examples thereof include the same compounds as in the A Since the C is an aromatic hydrocarbon group having one ring or a heteroaromatic group having one ring, the affinity for the electron accepting organic semiconductor which is often a conjugated material, is enhanced. Among these ring structures, a benzene ring is preferred as C from the viewpoint of stability, versatility and easy handleability.

In general formula (3), $R_3$s are n of substituents coupled with the C at an arbitrary position, may be the same or different, and represent an alkyl group, an alkoxy group, an alkanoyl group or a thioalkyl group. The alkyl group, the alkoxy group, the alkanoyl group and the thioalkyl group are similar to those in the above-mentioned $R_1$ and $R_2$. A plurality of $R_2$s may be combined with one another to form a ring.

Further, at least one among $R_3$s is a thioalkyl group. By having one or more thioalkyl groups as the substituent, the affinity of the additive for the electron accepting organic semiconductor is enhanced and dispersibility of the electron accepting organic semiconductor is improved. From the viewpoint of the affinity of the additive for the electron accepting organic semiconductor, a compound in which in formula (3), n is 1 and $R_3$ is a thioalkyl group is more preferred. Moreover, a compound in which n is 2 or more and at least one $R_3$ is an alkoxy group, is also preferably used. Further, the thioalkyl group is preferably shorter in a length so that a density at a site having high affinity for the electron accepting organic semiconductor is not decreased and, therefore, the thioalkyl group is more preferably a methylthio group.

In addition, the reason why the number of substitutions (n) of the C of 1 or more is sufficient in the compound of formula (3) and the number of substitutions is allowed to be smaller than the number of substitutions (2 or more) of the A in the compound of formula (1) is supposedly that since the C is substituted with a thioalkyl group, it has the affinity for the electron accepting organic semiconductor higher than the A being substituted with an alkoxy group or an alkanoyl group due to the effect of a magnitude of an electron orbit of a sulfur atom or the like.

Specific examples of the compounds represented by formula (3) include thioanisole, ethyl phenyl sulfide, 4-(methylthio)toluene and its position isomers thereof, 2-methoxythioanisole and its position isomers thereof, 2,3-dihydro-1-benzothiophene, position isomers of bis(methylthio)benzene, and the like. However, these compounds are examples, and the compound represented by formula (3) is not limited to these compounds.

In addition, an exact mechanism of an improvement of performance by the additive is not clear. However, we believe that an additive having high affinity for the electron accepting organic semiconductor suppresses the aggregation of the electron accepting organic semiconductor to control a phase-separation structure in the process in which the organic semiconductor composition containing an additive is dried/condensed. From this, it is necessary that a boiling point of the additive is higher than a boiling point of a solvent. Since there is such a difference in a boiling point, we believe that a solvent is precedently removed during drying the organic semiconductor composition and a concentration of the additive having high affinity for the electron accepting organic semiconductor is gradually increased and, therefore, the aggregation of the electron accepting organic semiconductor is suppressed.

Accordingly, in the organic semiconductor composition, when a composition other than an electron donating and an electron accepting organic semiconductors is only compounds represented by any one of formulae (1) to (3), a compound with a lower boiling point is considered as a solvent and a compound with a higher boiling point is considered as an additive. For example, when a composition other than the organic semiconductor is composed of 1,2-dimethoxybenzene and 1,2,4-trimethoxybenzene, both compounds are a compound represented by formula (1), and 1,2-dimethoxybenzene with a lower boiling point is considered as a solvent and 1,2,4-trimethoxybenzene with a higher boiling point is considered as an additive.

However, it is preferred that the boiling point is not excessively high since if the additive excessively remains after application/drying, there is apprehension that the remaining additive interferes with carrier transport as an insulator or reduces durability, and the boiling point, depending on volatility of the additive, is preferably 400° C. or lower. Moreover, since a lower limit of an additive boiling point also depends on a boiling point of a solvent used in combination, a lower boiling point is tolerated as a solvent having a low boiling point is used. However, the boiling point of the additive is preferably 200° C. or higher from the viewpoint that a variety of solvents such as a solvent with a high boiling point can be used. Further, the additive may be a liquid compound or may be a solid compound at ordinary temperatures and pressures.

The content of the additive is not particularly limited as long as it provides a uniform solution as the composition. When a boiling point of the solvent is close to that of the additive, the additive starts being dried almost as soon as the solvent is dried, and therefore the content of the additive is preferably as large as the additive remains in an amount enough to disperse the electron accepting organic semiconductor after the solvent is dried, and the additive content is preferably higher. However, when a large amount of an additive with a high boiling point is used, it becomes difficult to dry/remove it, and therefore an upper limit of the additive content is preferably 50% by mass, more preferably 20% by mass, and furthermore preferably 10% by mass with respect to the solvent. Further, when a boiling point of the solvent is remote from that of the additive, an adequate amount of the additive easily remains after the solvent is dried, and therefore the additive content may be small. However, even when a boiling point of the solvent is remote from that of the additive, it is possible that the solvent and the additive start being dried simultaneously due to azeotropy or volatility depending on chemical structures of the solvent and the additive and, therefore, a lower limit of the additive content is preferably 0.01% by mass, more preferably 0.1% by mass and, furthermore, preferably 1% by mass with respect to the solvent.

In addition, the composition may contain other components such as a surfactant, a binder resin or a filler in addition to the electron donating organic semiconductor, the electron accepting organic semiconductor, the solvent and the additive within a range which does not impair the desired object.

The solvent and additive, depending on a treatment step after applying a solution, may remain in a trace amount in an applied film, and this can be detected by an appropriate remaining-solvent analysis method. Examples of such a remaining-solvent analysis method include an analysis method of gas generation by heating, and a solvent remaining in a trace amount in an applied film can be detected by using thermogravimetry-mass spectrometry (TG-MS), temperature programmed desorption-mass spectrometry (TPD-MS), thermal desorption spectrometry (TDS), purge & trap-gas chromatography-mass spectrometry (P&T-GC-MS), or GC-MS analysis of a dissolved product (a power generation layer is redissolved and then GC-MS is carried out).

Photovoltaic Element

Next, the photovoltaic element will be described.

The photovoltaic element has a photoelectric conversion layer formed by drying the above-mentioned organic semiconductor composition formed between an anode and a cathode at least one of which has light transmittance. FIG. 1 is a sectional view showing one aspect of a photovoltaic element. The photovoltaic element of FIG. 1 has an anode 2, a hole extraction layer 3, a photoelectric conversion layer 4, an electron extraction layer 5, and a cathode 6 in this order on a substrate 1.

Depending on the kinds and usages of the photoelectric conversion material, the substrate 1 may be formed as a substrate on which an electrode material and an organic semiconductor layer can be stacked and, for example, a film or a plate prepared by using any method from an inorganic material such as non-alkali glass, quartz glass, aluminum, iron, copper or an alloy such as stainless steel, or an organic material such as polyester, polycarbonate, polyolefin, polyamide, polyimide, polyphenylene sulfide, polyparaxylene-polymethyl methacrylate, an epoxy resin, or a fluorine-based resin, can be used. Further, when incident light from the substrate side is used, it is preferred that each of the above-mentioned substrates preferably has a light-transmitting property of about 80%.

The electrodes (anode 2 and cathode 6) are made of a conductive material, and examples of a material preferably used as an electrode material include metals such as gold, platinum, silver, copper, iron, zinc, tin, aluminum, indium, chromium, nickel, cobalt, scandium, vanadium, yttrium, cerium, samarium, europium, terbium, ytterbium, molybdenum, tungsten, and titanium; metal oxides; composite metal oxides (indium tin oxide (ITO), indium zinc oxide (IZO), aluminum zinc oxide (AZO), gallium zinc oxide (GZO) and the like); alkali metals and alkaline-earth metals (lithium, magnesium, sodium, potassium, calcium, strontium and barium). Moreover, electrodes composed of alloys made from these metals or laminates of these metals are also preferably used. An electrode containing graphite, a graphite intercalation compound, a carbon nanotube, graphene, polyaniline or its derivatives, or polythiophene or its derivatives is also preferably used. The electrode may have a form of a mixed layer or a stacked structure respectively made from two or more materials.

The conductive materials to be used for the anode 2 and the cathode 6 are preferably a compound to form ohmic junction with the neighboring hole extraction layer 3 and the neighboring electron extraction layer 5, respectively.

At least one of the anode 2 and the cathode 6 of the photovoltaic element has a light-transmitting property. At least either the anode or the cathode may have a light-transmitting property, and both of them may have a light-transmitting property. The term "having a light-transmitting property" means to transmit light to a level at which an electromotive force is generated by incident light arrival at the photoelectric conversion layer. That is, when the electrode has a light transmittance more than 0%, it is assumed that the electrode has a light-transmitting property. The electrode having the light-transmitting property preferably has a light transmittance of 60-100% in a region of all wavelengths of 400 nm or more and 900 nm or less. Further, the thickness of the electrode having the light-transmitting property may be one at which sufficient conducting properties can be achieved, and the thickness is preferably 20 nm to 300 nm, differing depending on an electrode material. In addition, the electrode not having the light-transmitting property is enough if having conducting properties, and the thickness thereof is not particularly limited.

The hole extraction layer 3 is not essential for the photovoltaic element. However, since an interface state suitable for extracting a carrier can be formed and short-circuit between electrodes is prevented by disposing the hole extraction layer 3, it is preferred to dispose the hole extraction layer 3. Examples of a material to form the hole extraction layer preferably used include conductive polymers such as a polythiophene-based polymer, a poly-p-phenylenevinylene-based polymer, a polyfluorene-based polymer, a polypyrrole polymer, a polyaniline polymer, a polyfuran polymer, a polypyridine polymer, and a polycarbazole polymer; low-molecular weight organic compounds exhibiting p-type semiconductor characteristics such as phthalocyanine derivatives ($H_2Pc$, CuPc, ZnPc and the like), porphyrin derivatives, and acene-based compounds (tetracene, pentacene and the like); carbon compounds such as carbon nanotubes, graphene and graphene oxide; and inorganic compounds including molybdenum oxide ($MoO_x$) such as $MoO_3$, tungsten oxide ($WO_x$) such as $WO_3$, nickel oxide ($NiO_x$) such as NiO, vanadium oxide ($VO_x$) such as $V_2O_5$, zirconium oxide ($ZrO_x$) such as $ZrO_2$, copper oxide ($CuO_x$) such as $Cu_2O$, copper iodide, ruthenium oxide ($RuO_x$) such as $RuO_4$, and ruthenium oxide ($ReO_x$) such as $Re_2O_7$. Particularly, polyethylenedioxythiophene (PEDOT) serving as a polythiophene-based polymer, those materials prepared by adding polystyrene sulfonate (PSS) to PEDOT, molybdenum oxide, vanadium oxide and tungsten oxide, are preferably used. The hole transporting layer may be a layer made of a single compound, or may be a mixed layer or a stacked structure respectively made of two or more compounds.

The thickness of the hole transporting layer is preferably 5 nm to 600 nm, and more preferably 10 nm to 200 nm.

Next, the photoelectric conversion layer 4 will be described. The photoelectric conversion layer 4 exists between the anode 2 and the cathode 6, and is a layer formed by applying the above-mentioned organic semiconductor composition. A structure of the photoelectric conversion layer may be only a layer made of a mixture of the electron donating organic semiconductor and the electron accepting organic semiconductor; and a stacked structure of the layer made of the electron donating organic semiconductor, the layer made of the electron accepting organic semiconductor and the layer made of the mixture of these two materials and interposed between these two layers. The photoelectric conversion layer may contain two or more kinds of the electron donating organic semiconductor or the electron accepting organic semiconductor.

The content ratio of the electron donating organic semiconductor and the electron accepting organic semiconductor in the photoelectric conversion layer is not particularly limited. However, the ratio by weight between the electron donating organic semiconductor and the electron accepting organic semiconductor is preferably 1 to 99:99 to 1, more preferably 10 to 90:90 to 10, and furthermore preferably 20 to 60:80 to 40.

The photoelectric conversion layer may have a thickness enough to generate a photovoltaic power based on optical absorption of the electron donating organic semiconductor and the electron accepting organic semiconductor. The photoelectric conversion layer preferably has a thickness of 10 nm to 1000 nm, more preferably 50 nm to 500 nm, differing depending on a photoelectric conversion layer material. Further, the photoelectric conversion layer may contain other components such as a surfactant, a binder resin or a filler.

The electron extraction layer 5 is not essential for the photovoltaic element. However, since an interface state suitable for extracting a carrier can be formed and short-circuit between electrodes is prevented by disposing the electron extraction layer 5, it is preferred to dispose the electron extraction layer 5. Examples of the material preferably used to form the electron extraction layer include organic materials exhibiting n-type semiconductor characteristics such as the above-mentioned electron accepting organic materials (NTCDA, PTCDA, PTCDI-C8H, oxazole derivatives, triazole derivatives, phenanthroline derivatives, phosphine oxide derivatives, phosphine sulfide derivatives, quinoline derivatives, fullerene compounds, CNT, CN-PPV and the like.). Further, ionic compounds such as an ionic substituted fluorene polymer ("Advanced Materials," Vol. 23, pp. 4636-4643, 2011, "Organic Electronics," Vol. 10, pp. 496-500, 2009) and a combination of the ionic substituted fluorene polymer and a substituted thiophene polymer ("Journal of American Chemical Society," Vol. 133, pp. 8416-8419, 2011), polyethylene oxide ("Advanced Materials," Vol. 19, pp. 1835-1838, 2007) and the like can also be used as the electron extraction layer. Further, ionic compounds such as an ionic substituted fluorene polymer ("Advanced Materials," Vol. 23, pp. 4636-4643, 2011, "Organic Electronics," Vol. 10, pp. 496-500, 2009) and a combination of the ionic substituted fluorene polymer and a substituted thiophene polymer ("Journal of American Chemical Society," Vol. 133, pp. 8416-8419, 2011), polyethylene oxide ("Advanced Materials," Vol. 19, pp. 1835-1838, 2007) and the like can also be used as the electron extraction layer. Moreover, compounds having ionic groups such as ammonium salt, amine salt, pyridinium salt, imidazolium salt, phosphonium salt, carboxylate salt, sulfonate salt, phosphate salt, sulfuric acid ester salt, phosphoric acid ester salt, sulfate salt, nitrate salt, acetonate salt, oxo acid salt and a metal complex, can also be used as the electron transporting layer.

Specific examples thereof include ammonium chloride, ammonium acetate, ammonium phosphate, hexyltrimethylammonium bromide, tetrabutylammonium bromide, octadecyltrimethylammonium bromide, hexadecylpyridinium bromide, 1-butyl-3-methylimidazolium bromide, tributylhexadecylphosphonium bromide, zinc formate, zinc acetate, zinc propionate, zinc butyrate, zinc oxalate, sodium heptadecafluorononanate, sodium myristate, sodium benzoate, sodium 1-hexadecanesulfonate, sodium dodecyl sulfate, sodium monododecyl phosphate, zinc acetylacetonate, ammonium chromate, ammonium metavanadate, ammonium molybdate, ammonium hexafluorozirconate, sodium tungstate, ammonium tetrachlorozincate, tetraisopropyl orthotitanate, lithium nickelate, potassium permanganate, silver phenanthroline complex, AgTCNQ, and compounds used for the electron transporting layer, which is described in Japanese Patent Laid-open Publication No. 2013-58714.

Also, inorganic materials, for example, metal oxides including titanium oxide ($TiO_x$) such as $TiO_2$, zinc oxide ($ZnO_x$) such as ZnO, silicon oxide ($SiO_x$) such as $SiO_2$, tin oxide ($SnO_x$) such as $SnO_2$, tungsten oxide ($WO_x$) such as $WO_3$, tantalum oxide ($TaO_x$) such as $Ta_2O_3$, barium titanate ($BaTi_xO_y$) such as $BaTiO_3$, barium zirconate ($BaZr_xO_y$) such as $BaZrO_3$, zirconium oxide ($ZrO_x$) such as $ZrO_2$, hafnium oxide ($HfO_x$) such as $HfO_2$, aluminum oxide ($AlO_x$) such as $Al_2O_3$, yttrium oxide ($YO_x$) such as $Y_2O_3$ and zirconium silicate ($ZrSi_xO_y$) such as $ZrSiO_4$; nitrides including silicon nitride ($SiN_x$) such as $Si_3N_4$; and semiconductors including cadmium sulfide ($CdS_x$) such as CdS, zinc selenide ($ZnSe_x$) such as ZnSe, zinc sulfide ($ZnS_x$) such as ZnS, and cadmium telluride ($CdTe_x$) such as CdTe, are preferably used.

Examples of a method of forming the electron extraction layer by using the above-mentioned inorganic material include a method in which a solution of a precursor of metal salt or metal alkoxide of the inorganic material is applied and then heated to form a layer, and a method of forming a layer by applying a dispersion of nanoparticles onto a substrate. In this case, depending on a heating temperature and time and a synthesis condition of nanoparticles, a reaction does not have to proceed completely, and the precursor may be partially hydrolyzed or partially condensed to become an intermediate product or become a mixture of the precursor, the intermediate product and a final product.

Examples of another aspect of the photovoltaic element include a structure in which the element has a cathode, an electron extraction layer, a photoelectric conversion layer, a hole extraction layer, and an anode in this order on a substrate.

As the photovoltaic element, two or more photoelectric conversion layers may be stacked (into a tandem structure), with one or more charge recombination layers interposed therebetween to form series junctions. For example, the stacked layer structure includes: substrate/anode/first hole extraction layer/first photoelectric conversion layer/first electron extraction layer/charge recombination layer/second hole extraction layer/second photoelectric conversion layer/second electron extraction layer/cathode, and the stacked layer structure includes: substrate/cathode/first electron extraction layer/first photoelectric conversion layer/charge recombination layer/second electron extraction layer/second photoelectric conversion layer/anode. In this case, it is possible that the charge recombination layer also serves as a cathode and an anode of the neighboring photoelectric conversion layer. By using this stacked layer structure, it becomes possible to improve an open voltage.

The charge recombination layer used herein needs to have a light-transmitting property so that a plurality of photoelectric conversion layers can perform optical absorption. Further, since the charge recombination layer may be designed to adequately recombine the hole with the electron, it is not necessarily a film and may be, for example, a metal cluster which is uniformly formed on the photoelectric conversion layer. Accordingly, as the charge recombination layer, very thin metal films or metal clusters (including alloys) composed of the above-mentioned gold, platinum, chromium, nickel, lithium, magnesium, calcium, tin, silver or aluminum, and has a thickness of about several angstroms to several tens of angstroms and a light-transmitting property; films and clusters of metal oxide having a high light-transmitting property such as ITO, IZO, AZO, GZO, FTO, titanium oxide and molybdenum oxide; films of conductive organic materials such as PEDOT to which PSS is added; or composite materials thereof are used. For example, when silver is evaporated onto a quartz oscillator type film thickness monitor to be several angstroms to 1 nm in thickness by using a vacuum vapor deposition method, a uniform silver cluster can be formed. In addition to this, when a titanium oxide film is formed, a sol-gel method which is described in "Advanced Materials," Volume 18, pp. 572-576, 2006 may be used. When a composite metal oxide such as ITO or IZO is used, a film may be formed by using a sputtering method. A forming method or the kinds of these charge recombination layer may be appropriately selected in consideration of the non-destructivity against the photoelectric conversion layer in forming the charge recombination layer or the forming method of a next photoelectric conversion layer to be stacked.

Methods of Manufacturing Organic Semiconductor Composition and Photovoltaic Element Next, methods of manufacturing an organic semiconductor composition and a photovoltaic element will be described by way of examples.

The organic semiconductor composition is obtained by dissolving the electron donating organic semiconductor and the electron accepting organic semiconductor, by using a method such as heating, stirring, or irradiating with ultrasonic wave, in a solvent to which an additive is added.

In manufacturing the photovoltaic element, first, a transparent electrode (in this case, corresponding an anode) such as ITO is formed on a substrate by a sputtering method or the like. Then, the organic semiconductor composition is applied onto the transparent electrode to form a photoelectric conversion layer.

The photoelectric conversion layer may be formed by using any of the following methods: a spin coating method, a blade coating method, a slit die coating method, a screen printing method, a bar coating method, a mold coating method, a print transfer method, a dip coating method, an ink-jet method, a spraying method, and the like, and the coating method may be selected according to the characteristics of a coating to be obtained such as coating-thickness controlling and orientation controlling.

Then, to remove the solvent and the additive from the formed coating, the organic semiconductor composition may be dried under reduced pressure or may be subjected to heating/drying (in the atmosphere, in an atmosphere of an inert gas (in a nitrogen or argon atmosphere, under reduced pressure)). The temperature of the heating/drying treatment is preferably 4° C. to 200° C., and more preferably 50° C. to 150° C.

Next, a metal electrode (corresponding to a cathode, in this case) made of Al or the like is formed on the photoelectric conversion layer by a vacuum vapor deposition method, a sputtering method or the like. When an electron extraction layer is formed by the vacuum vapor deposition, the metal electrode is preferably formed, with the vacuum state being successively maintained.

When a hole extraction layer and an electron extraction layer are disposed between the electrode and the photoelectric conversion layer, a desired material (PEDOT:PSS or the like) is applied onto the photoelectric conversion layer by a spin coating method, a bar coating method, or a casting method by the use of a blade, and then the solvent is removed by using a vacuum thermostat, a hot plate or the like to form the hole extraction layer and the electron extraction layer. For an application method, the same method as in the above-mentioned formation of a photoelectric conversion layer can be used. When a low-molecular weight organic material such as phthalocyanine derivatives or porphyrin derivatives or an inorganic material such as molybdenum oxide or tungsten oxide, is used, a vacuum vapor deposition method or a sputtering method can also be applicable.

The photovoltaic element can be applicable to various photoelectric conversion devices in which its photoelectric conversion function, photo-rectifying function, or the like is utilized. For example, it is useful for photoelectric cells (solar cells or the like), electron devices (such as a photosensor, photoswitch, phototransistor or the like), photorecording materials (photomemory or the like), imaging devices and the like.

EXAMPLES

Hereinafter, our compositions, elements, devices and methods will be described in more detail based on examples. In addition, this disclosure is not intended to be limited by the following examples. Also, among compounds which are used in the examples, those indicated by abbreviations are shown below:
Isc: Short-circuit current density
Voc: Open circuit voltage
FF: Fill factor
η: Photoelectric conversion efficiency
ITO: Indium tin oxide
[70]PCBM: Phenyl C71 butyric acid methyl ester.

Photoelectric conversion efficiency in Examples/Comparative Examples was determined by the following formula:

η(%)=Isc (mA/cm$^2$)×Voc (V)×FF/Intensity of irradiation light (mW/cm$^2$)×100

FF=$JV$max/(Isc (mA/cm$^2$)×Voc (V))

wherein JVmax (mW/cm$^2$) corresponds to a value of product of the electric current density and the applied voltage at a point where the product of the electric current density and the applied voltage becomes the largest between 0 V of the applied voltage and the open circuit voltage value.

Synthesis Example 1

A compound A-1 was synthesized by the method shown in a formula 1. In addition, a compound (1-i) and a compound (1-p) described in Synthesis Example 1 were synthesized by reference to a method described in "Journal of the American Chemical Society," Vol. 131, pp. 7792-7799, 2009, and a method described in "Angewandte Chem International Edition," Vol. 50, pp. 9697-9702, 2011, respectively.

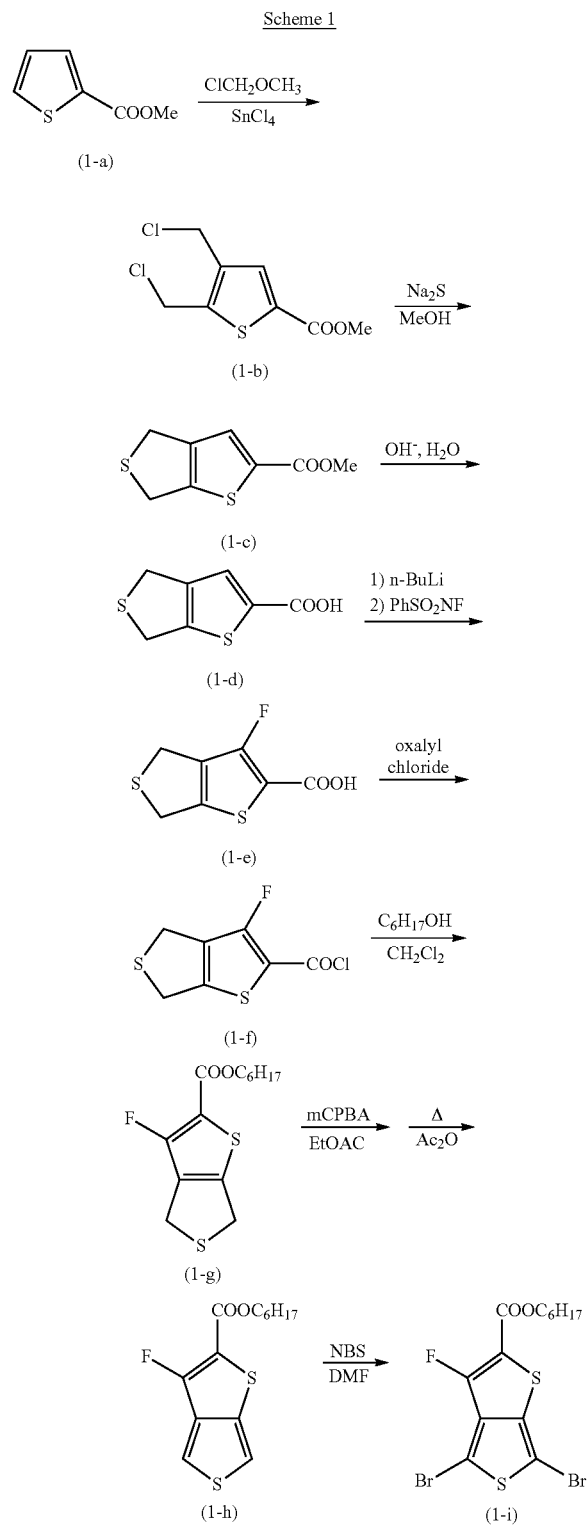

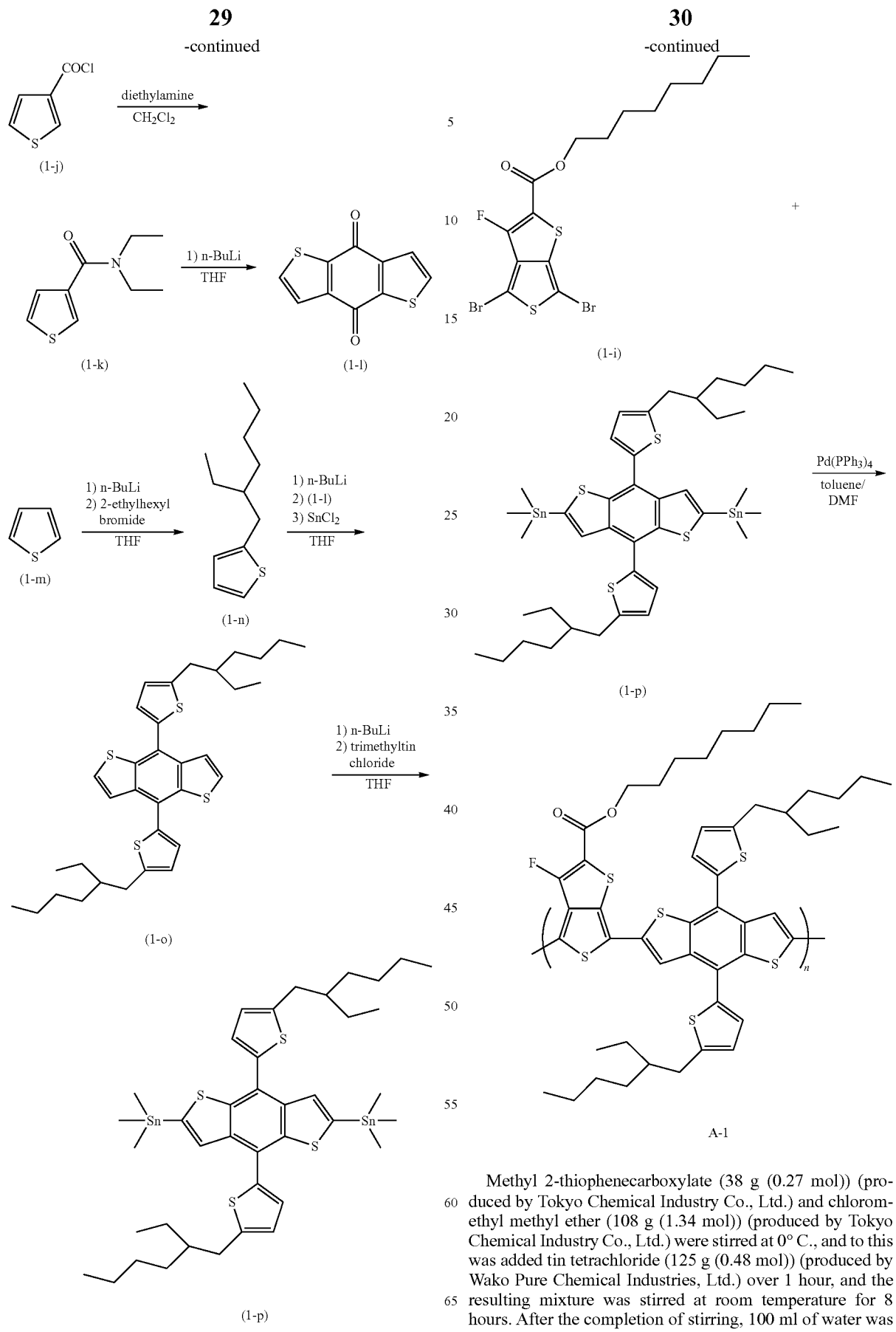

Methyl 2-thiophenecarboxylate (38 g (0.27 mol)) (produced by Tokyo Chemical Industry Co., Ltd.) and chloromethyl methyl ether (108 g (1.34 mol)) (produced by Tokyo Chemical Industry Co., Ltd.) were stirred at 0° C., and to this was added tin tetrachloride (125 g (0.48 mol)) (produced by Wako Pure Chemical Industries, Ltd.) over 1 hour, and the resulting mixture was stirred at room temperature for 8 hours. After the completion of stirring, 100 ml of water was added gradually at 0° C., and the resulting mixture extracted with chloroform three times. The resulting organic layer was washed with a saturated saline, the solvent dried with anhydrous magnesium sulfate, and then removed under reduced pressure. The resulting brown solid was recrystallized from methanol to obtain a compound (1-b) as a light yellow solid (24.8 g, yield 39%). The result of $^1$H-NMR measurement on compound (1-b) is shown below: $^1$H-NMR (270 MHz, CDCl$_3$): 7.71 (s, 1H), 4.79 (s, 1H), 4.59 (s, 1H), 3.88 (s, 3H) ppm.

The compound (1-b) (24.8 g (0.10 mmol)) was dissolved in methanol (1.2 L) (produced by SASAKI CHEMICAL CO., LTD.) and stirred at 60° C., and to this was added dropwise a methanol solution (100 ml) of sodium sulfide (8.9 g (0.11 mol)) (produced by Aldrich Chemical Co.) over 1 hour, and the resulting mixture was stirred at 60° C. for 4 hours. After completion of a reaction, the solvent was removed under reduced pressure, 200 ml of chloroform and 200 ml of water added, and the resulting insoluble matter was separated by filtration. The resulting organic layer was washed with water two times and with a saturated saline once, and dried with anhydrous magnesium sulfate, and then the solvent was removed under reduced pressure. A roughly-purified product was refined by silica-gel column chromatography (eluent, chloroform) to obtain a compound (1-c) as a white solid (9.8 g, yield 48%). The result of $^1$H-NMR measurement on compound (1-c) is shown below:

$^1$H-NMR (270 MHz, CDCl$_3$): 7.48 (s, 1H), 4.19 (t, J=3.0 Hz, 2H), 4.05 (t, J=3.0 Hz, 2H), 3.87 (s, 3H) ppm.

To the compound (1-c) (9.8 g (49 mmol)) were added water (100 ml) and then a 3 M aqueous sodium hydroxide solution (30 ml), and the resulting mixture was stirred at 80° C. for 4 hours. After completion of a reaction, 15 ml of a concentrated hydrochloric acid was added at 0° C., the resulting deposited solid matter separated by filtration and washed with water several times. The resulting solid matter was dried to obtain a compound (1-d) as a white solid (8.9 g, yield 98%).

$^1$H-NMR (270 MHz, DMSO-d$_6$): 7.46 (s, 1H), 4.18 (t, J=3.2 Hz, 2H), 4.01 (t, J=3.2 Hz, 2H) ppm.

The compound (1-d) (1.46 g (7.8 mmol)) was dissolved in 60 ml of a dehydrated tetrahydrofuran (produced by Wako Pure Chemical Industries, Ltd.) and stirred at −78° C., and to this was added dropwise a n-butyllithium hexane solution (10.7 ml (17.2 mmol)) (1.6 M, produced by Wako Pure Chemical Industries, Ltd.), and the resulting mixture was stirred at −78° C. for 1 hour. Then, a dried tetrahydrofuran solution (20 ml) of N-fluorobenzene sulfonimide (4.91 g (15.6 mmol)) (produced by Tokyo Chemical Industry Co., Ltd.) was added dropwise at −78° C. over 10 minutes, and the resulting mixture stirred at room temperature for 12 hours. After completion of a reaction, 50 ml of water was added gradually. A 3 M hydrochloric acid solution was added to allow a water layer to be acid, and then the resulting mixture extracted with chloroform three times. After an organic layer was dried with anhydrous magnesium sulfate, the solvent was distilled off under reduced pressure. After a by-product was removed by silica-gel column chromatography (eluent, ethyl acetate), the resulting product was re-crystallized from ethyl acetate to obtain a compound (1-e) as a light yellow powder (980 mg, yield 61%). The result of $^1$H-NMR measurement on compound (1-e) is shown below:

$^1$H-NMR (270 MHz, DMSO-d$_6$): 13.31 (brs, 1H), 4.20 (t, J=3.0 Hz, 2H), 4.03 (t, J=3.0 Hz, 2H) ppm.

To 10 ml of a dehydrated dichloromethane (produced by Wako Pure Chemical Industries, Ltd.) solution of the compound (1-e) (800 mg (3.9 mmol)) were added oxalyl chloride (1 ml) (Tokyo Chemical Industry Co., Ltd.) and then dimethylformamide (one drop) (produced by Wako Pure Chemical Industries, Ltd.), and the resulting mixture was stirred at room temperature for 3 hours. The solvent and excessive oxalyl chloride were removed under reduced pressure to obtain a compound (1-f) as a yellow oil. The compound (1-f) was used for a subsequent reaction as-is.

A dichloromethane solution (10 ml) of the compound (1-f, roughly-refined product) was added to a dichloromethane solution (15 ml) of 1-octanol (1.3 g (10 mmol)) (produced by Wako Pure Chemical Industries, Ltd.) and triethylamine (800 mg (8 mmol)) (produced by Wako Pure Chemical Industries, Ltd.) at room temperature, and the resulting mixture was stirred at room temperature for 6 hours. The resulting reaction solution was washed with a 1 M hydrochloric acid solution two times, with water once and with a saturated saline once, and dried with anhydrous magnesium sulfate, and then the solvent was distilled off under reduced pressure. The resulting product was refined by silica-gel column chromatography (eluent, chloroform) to obtain a compound (1-g) as a light yellow solid (1.12 g, yield 90%). The result of $^1$H-NMR measurement on compound (1-g) is shown below:

$^1$H-NMR (270 MHz, CDCl$_3$): 4.27 (t, J=6.7 Hz, 2H), 4.16 (t, J=3.0 Hz, 2H), 4.01 (t, J=3.0 Hz, 2H), 1.72 (m, 2H), 1.5-1.3 (m, 12H), 0.88 (t, J=7.0 Hz, 3H) ppm.

To 40 ml of an ethyl acetate solution of the compound (1-g) (1.1 g (3.5 mmol)) was added dropwise an ethyl acetate solution (10 ml) of m-chlorobenzoic acid (630 mg (3.6 mmol)) (produced by Nacalai Tesque Inc.) at 0° C., and the resulting mixture was stirred at room temperature for 5 hours. After the solvent was removed under reduced pressure, 30 ml of acetic acid anhydride was added, and the resulting mixture heated/refluxed for 3 hours. After the solvent was removed again under reduced pressure, the resulting product was refined by silica-gel column chromatography (eluent, dichloromethane:hexane=1:1) to obtain compound (1-h) as a light yellow oil (1.03 g, yield 94%). The result of $^1$H-NMR measurement on compound (1-h) is shown below:

$^1$H-NMR (270 MHz, CDCl$_3$): 7.65 (d, J=2.7 Hz, 1H), 7.28 (dd, J=2.7 Hz and 5.4 Hz, 1H), 4.31 (t, J=6.8 Hz, 2H), 1.75 (m, 2H), 1.42-1.29 (m, 12H), 0.89 (t, J=6.8 Hz, 3H) ppm.

To 20 ml of a dimethylformamide solution of the compound (1-h) (1.0 g (3.2 mmol)) was added N-bromosuccinimide (1.25 g (7.0 mmol)) (produced by Wako Pure Chemical Industries, Ltd.) at room temperature, and the resulting mixture stirred at room temperature for 3 hours. After completion of a reaction, 10 ml of a 5% aqueous sodium thiosulfate solution was added, and the resulting mixture stirred for 5 minutes. Then, 80 ml of ethyl acetate was added, and the resulting organic layer washed with water five times and with a saturated saline once, and dried with anhydrous magnesium sulfate, and then the solvent was distilled off under reduced pressure. The resulting product was refined by silica-gel column chromatography (eluent, chloroform:hexane=1:3) to obtain a compound (1-i) as a light yellow solid (1.2 g, yield 79%). The result of $^1$H-NMR measurement on compound (1-i) is shown below: $^1$H-NMR (270 MHz, CDCl$_3$): 4.32 (t, J=6.5 Hz, 2H), 1.75 (m, 2H), 1.42-1.29 (m, 12H), 0.89 (t, J=6.8 Hz, 3H) ppm.

To 300 ml of a dichloromethane solution of diethylamine (110 g (1.5 mol)) (produced by Wako Pure Chemical Industries, Ltd.) was added 3-thiophenecarbonyl chloride (100 g (0.68 mol)) (produced by Wako Pure Chemical Industries, Ltd.) at 0° C. over 1 hour, and the resulting mixture stirred at 0° C. for 3 hours. After completion of stirring, 200 ml of water was added, and the resulting organic layer washed with water three times and with a saturated saline once. After the organic layer was dried with anhydrous magnesium sulfate, the solvent was distilled off under reduced pressure. A residue was distilled under reduced pressure to obtain a compound (1-k) as a light orange-colored liquid (102 g, yield 82%). The result of $^1$H-NMR measurement on compound (1-k) is shown below:

$^1$H-NMR (270 MHz, CDCl$_3$): 7.47 (dd, J=3.2 Hz and 1.0 Hz, 1H), 7.32 (dd, J=5.0 Hz and 3.2 Hz, 1H), 7.19 (dd, J=5.0 Hz and 1.0 Hz, 1H), 3.43 (brs, 4H), 1.20 (t, J=6.5 Hz, 6H) ppm.

To 400 ml of a dehydrated tetrahydrofuran (produced by Wako Pure Chemical Industries, Ltd.) solution of the compound (1-k) (73.3 g (0.40 mol)) was added dropwise a n-butyllithium hexane solution (250 ml (0.40 mol)) (1.6 M, produced by Wako Pure Chemical Industries, Ltd.) at 0° C. over 30 minutes. After the dropwise addition, the resulting mixture was stirred at room temperature for 4 hours. After completion of stirring, 100 ml of water was added gradually, and the resulting reaction mixture stirred for a while and then poured in 800 ml of water. The resulting deposited solid was separated by filtration and washed with water, methanol and then hexane to obtain a compound (1-1) as a yellow solid (23.8 g, yield 27%). The result of $^1$H-NMR measurement on compound (1-1) is shown below:

$^1$H-NMR (270 MHz, CDCl$_3$): 7.69 (d, J=4.9 Hz, 2H), 7.64 (d, J=4.9 Hz, 2H) ppm.

To 400 ml of a dehydrated tetrahydrofuran (produced by Wako Pure Chemical Industries, Ltd.) solution of thiophene (42 g (0.50 mol)) was added dropwise a n-butyllithium hexane solution (250 ml (0.40 mol)) (1.6 M, produced by Wako Pure Chemical Industries, Ltd.) at −78° C. over 30 minutes. After the resulting reaction mixture was stirred at −78° C. for 1 hour, 2-ethylhexylbromide (76.4 g (0.40 mol)) (produced by Wako Pure Chemical Industries, Ltd.) was added dropwise at −78° C. over 15 minutes. After the resulting reaction solution was stirred at room temperature for 30 minutes, it was heated and stirred at 60° C. for 6 hours. After completion of stirring, the reaction solution was cooled to room temperature, and to this were added 200 ml of water and 200 ml of ether. The resulting organic layer was washed with water two times and washed with a saturated saline, and dried with anhydrous magnesium sulfate, and then the solvent was distilled off under reduced pressure. A residue was distilled under reduced pressure to obtain a compound (1-n) as a colorless liquid (28.3 g, 36%). The result of $^1$H-NMR measurement on compound (1-n) is shown below:

$^1$H-NMR (270 MHz, CDCl$_3$): 7.11 (d, 4.9 Hz, 1H), 6.92 (dd, 4.9 Hz and 3.2 Hz, 1H), 6.76 (d, J=3.2 Hz, 1H), 2.76 (d, J=6.8 Hz, 2H), 1.62 (m, 1H), 1.4-1.3 (m, 8H), 0.88 (m, 6H) ppm.

To 400 ml of a dehydrated tetrahydrofuran (produced by Wako Pure Chemical Industries, Ltd.) solution of the compound (1-n) (17.5 g (89 mmol)) was added dropwise a n-butyllithium hexane solution (57 ml (89 mmol)) (1.6 M, produced by Wako Pure Chemical Industries, Ltd.) at 0° C. over 30 minutes. After the resulting reaction solution was stirred at 50° C. for 1 hour, the compound (1-1) (4.9 g (22 mmol)) was added at 50° C. and the resulting mixture stirred for 1 hour as-is. After completion of stirring, the reaction solution was cooled to 0° C., and to this was added a solution formed by dissolving tin chloride dihydrate (39.2 g (175 mmol)) (produced by Wako Pure Chemical Industries, Ltd.) in a 10% hydrochloric acid solution (80 mL), and the resulting mixture was stirred at room temperature for 1 hour. After completion of stirring, 200 ml of water and 200 ml of diethyl ether were added, and the resulting organic layer washed with water two times and washed with a saturated saline. After the organic layer was dried with anhydrous magnesium sulfate, the solvent was distilled off under reduced pressure. The resulting product was refined by silica-gel column chromatography (eluent, hexane) to obtain a compound (1-o) as a yellow oil (7.7 g, yield 59%). The result of $^1$H-NMR measurement on compound (1-o) is shown below:

$^1$H-NMR (270 MHz, CDCl$_3$): 7.63 (d, J=5.7 Hz, 1H), 7.45 (d, J=5.7 Hz, 1H), 7.29 (d, J=3.6 Hz, 1H), 6.88 (d, J=3.6 Hz, 1H), 2.86 (d, J=7.0 Hz, 2H), 1.70-1.61 (m, 1H), 1.56-1.41 (m, 8H), 0.97-0.89 (m, 6H) ppm.

To 25 ml of a dehydrated tetrahydrofuran (produced by Wako Pure Chemical Industries, Ltd.) solution of the compound (1-o) (870 mg (1.5 mmol)) was added a n-butyllithium hexane solution (2.0 ml (3.3 mmol)) (1.6 M, produced by Wako Pure Chemical Industries, Ltd.) at −78° C. by using a syringe, and the resulting mixture stirred at −78° C. for 30 minutes and at room temperature for 30 minutes. After the resulting reaction mixture was cooled to −78° C., trimethyltin chloride (800 mg (4.0 mmol)) (produced by Wako Pure Chemical Industries, Ltd.) was added at −78° C. at a time, and the resulting mixture stirred at room temperature for 4 hours. After completion of stirring, 50 ml of diethyl ether and 50 ml of water were added, and after the resulting mixture was stirred at room temperature for 5 minutes, the resulting organic layer was washed with water two times and washed with a saturated saline. After the solvent was dried with anhydrous sodium sulfate, the solvent was distilled off under reduced pressure. The resulting orange-colored oil was recrystallized from ethanol to obtain a compound (1-p) as a light yellow solid (710 mg, yield 52%). The result of $^1$H-NMR measurement on compound (1-p) is shown below:

$^1$H-NMR (270 MHz, CDCl$_3$): 7.68 (s, 2H), 7.31 (d, J=3.2 Hz, 2H), 6.90 (d, J=3.2 Hz, 2H), 2.87 (d, J=6.2 Hz, 4H), 1.69 (m, 2H), 1.40-1.30 (m, 16H), 1.0-0.9 (m, 12H), 0.39 (s, 18H) ppm.

The compound (1-i) (71 mg (0.15 mmol)) and the compound (1-p) (136 mg (0.15 mmol)) were dissolved in toluene (4 ml) (produced by Wako Pure Chemical Industries, Ltd.) and dimethylformamide (1 ml) (produced by Wako Pure Chemical Industries, Ltd.), and to this was added tetrakis (triphenyl phosphine) palladium (5 mg) (produced by Tokyo Chemical Industry Co., Ltd.), and the resulting mixture stirred at 100° C. for 15 hours in a nitrogen atmosphere. Next, to this was added 15 mg of bromobenzene (produced by Tokyo Chemical Industry Co., Ltd.), and the resulting mixture stirred at 100° C. for 1 hour. Then, 40 mg of tributyl(2-thienyl)tin (produced by Tokyo Chemical Industry Co., Ltd.) was added and the resulting mixture further stirred at 100° C. for 1 hour. After completion of stirring, the resulting reaction mixture was cooled to room temperature and poured in 100 ml of methanol. The resulting deposited solid matter was separated by filtration and washed with methanol, water and then acetone. Then, the solid matter was washed with acetone and hexane in this order using a Soxhlet extractor. Next, after the solid matter was dissolved in chloroform, and resulting chloroform solution passed through celite (produced by Nacalai Tesque Inc.) and subsequently through a silica-gel column (eluent: chloroform), the solvent was distilled off under reduced pressure. The resulting solid matter was dissolved in chloroform again, and then re-precipitated in methanol to obtain a compound A-1 (85 mg).

Synthesis Example 2

A compound E-1 was synthesized by the following method:

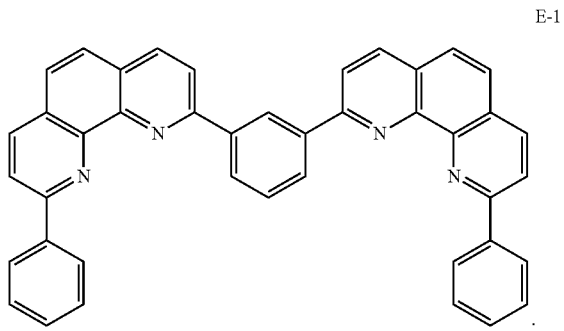 [SMILES: c1ccc(-c2ccc3ccc4ccc(-c5cccc(-c6ccc7ccc8ccc(-c9ccccc9)nc8c7n6)c5)nc4c3n2)cc1]

E-1

1,10-phenanthroline (9.64 g) was reacted with phenyl lithium (100 ml) (1.07 M cyclohexane/ether solution) at 0° C. for 1.5 hours in toluene (250 ml) and treated by a conventional method. The resulting product was reacted with manganese dioxide (93.0 g) at room temperature for 56 hours in dichloromethane (300 ml) and treated by a conventional method to obtain 9.44 g of 2-phenyl-1,10-phenanthroline. To 25 ml of a THF solution of 1,3-dibromobenzene (0.34 ml) was added an t-butyl lithium (1.53 M pentane solution) (7.35 mL) at −78° C., and the resulting mixture stirred for 1 hour, and then its temperature was raised to 0° C. The resulting solution was added to 85 ml of a THF solution of the obtained 2-phenyl-1,10-phenanthroline (1.44 g), and the resulting mixture was stirred at room temperature for 20 hours, and treated by a conventional method. The resulting product was reacted with manganese dioxide (8.50 g) at room temperature for 23 hours in dichloromethane (85 ml) and treated by a conventional method to obtain 1.08 g of a compound E-1.

Example 1

A chloroform solution (0.2 ml) (produced by Nacalai Tesque Inc., chloroform corresponds a solvent) containing 2,3-dihydrobenzofuran (produced by Tokyo Chemical Industry Co., Ltd., corresponding an additive) in an amount of 2% by mass, was added to a sample bottle containing 0.9 mg of A-1 (corresponding the electron donating organic semiconductor) and 1.1 mg of [70]PCBM (produced by Solenn Co., Ltd.), and further this was irradiated with ultrasonic waves for 30 minutes in an ultrasonic cleaning machine (US-2 manufactured by Iuchi Seieido Co., Ltd., output 120 W) to obtain a solution A.

A glass substrate on which an ITO transparent conductive layer serving as an anode was deposited by a sputtering method with a thickness of 125 nm was cut into a size of 38 mm×46 mm, and the ITO layer then patterned into a rectangular shape of 38 mm×13 mm by a photolithography method. Light transmittance of the resulting substrate was measured with a spectrophotometer U-3010 manufactured by Hitachi, Ltd., and consequently it was 85% or more in all wavelength region of 400 nm to 900 nm. The substrate was cleaned with ultrasonic waves for 10 minutes in an alkali cleaning solution ("Semicoclean" EL56, produced by Furuuchi Chemical Corporation), and then washed with ultrapure water. After this substrate was subjected to a UV/ozone treatment for 30 minutes, an aqueous PEDOT:PSS solution (CLEVIOS P VP AI4083) to be used to form a hole transporting layer was applied onto the substrate by a spin coating method and heated to dry at 200° C. for 5 minutes on a hot plate to form a hole extraction layer with a thickness of 30 nm. Next, the substrate and the above-mentioned solution A were transferred into a glove box in a nitrogen atmosphere, and subsequent steps to vapor deposition were performed without being brought into contact with the atmosphere. The above-mentioned solution A was added dropwise to the PEDOT:PSS layer, applied by a spin coating method, and heated to dry at 80° C. for 5 minutes on a hot plate to form to a photoelectric conversion layer having a thickness of 130 nm. Thereafter, the substrate with the photoelectric conversion layer formed thereon and a mask for a cathode were placed in a vacuum vapor deposition apparatus, and the apparatus was again evacuated until the degree of vacuum inside the apparatus reached $1 \times 10^{-3}$ Pa or less, and bathocuproine (produced by Luminescence Technology Corporation) and a lithium fluoride layer were vapor-deposited with thicknesses of 5 nm and 0.1 nm, respectively, by a resistive heating method. Thereafter, a silver layer serving as a cathode was vapor-deposited with a thickness of 100 nm. Thus, a photovoltaic element, in which an area of an intersection portion of the stripe-shaped ITO layer and the stripe-shaped silver is 5 mm×5 mm, was prepared.

The anode and cathode electrodes of the photovoltaic element thus prepared were connected to a 2400 series SourceMeter manufactured by TFF Corporation Keithley Instruments, and the element irradiated with simulated solar light (OTENTO-SUNIII manufactured by Bunkoukeiki Co., Ltd., spectral-shape: AM 1.5, Intensity: 100 mW/cm²) from the ITO layer side in the atmosphere, and the current value was measured, with the applied voltage being varied from −1 V to +2 V.

A photoelectric conversion efficiency ($\eta$) calculated from the resulting current values was 7.11%.

Example 2

A photovoltaic element was prepared and measured, and a photoelectric conversion efficiency calculated in the same manner as in Example 1 except for changing 2,3-dihydrobenzofuran to 3,5-dimethylanisole (produced by Tokyo Chemical Industry Co., Ltd.), and consequently the photoelectric conversion efficiency ($\eta$) was 7.47%.

Example 3

A photovoltaic element was prepared and measured, and a photoelectric conversion efficiency calculated in the same manner as in Example 1 except for changing 2,3-dihydrobenzofuran to 1-methoxynaphthalene (produced by Tokyo Chemical Industry Co., Ltd.), and consequently the photoelectric conversion efficiency ($\eta$) was 7.69%.

Example 4

A photovoltaic element was prepared and measured, and a photoelectric conversion efficiency calculated in the same manner as in Example 1 except for changing 2,3-dihydrobenzofuran to 1,3-dimethoxybenzene (produced by Tokyo Chemical Industry Co., Ltd.), and consequently the photoelectric conversion efficiency ($\eta$) was 8.38%.

Example 5

A photovoltaic element was prepared and measured, and a photoelectric conversion efficiency calculated in the same manner as in Example 1 except for changing 2,3-dihydrobenzofuran to 1,2-dimethoxybenzene (produced by Tokyo Chemical Industry Co., Ltd.), and consequently the photoelectric conversion efficiency ($\eta$) was 8.10%.

Example 6

A photovoltaic element was prepared and measured, and a photoelectric conversion efficiency calculated in the same manner as in Example 1 except for changing 2,3-dihydrobenzofuran to 1,4-benzodioxane (produced by Tokyo Chemical Industry Co., Ltd.), and consequently the photoelectric conversion efficiency ($\eta$) was 8.47%.

Example 7

A photovoltaic element was prepared and measured, and a photoelectric conversion efficiency calculated in the same manner as in Example 1 except for changing 2,3-dihydrobenzofuran to 3,4-dimethoxytoluene (produced by Tokyo Chemical Industry Co., Ltd.), and consequently the photoelectric conversion efficiency ($\eta$) was 8.43%.

Example 8

A photovoltaic element was prepared and measured, and a photoelectric conversion efficiency calculated in the same manner as in Example 1 except for changing 2,3-dihydrobenzofuran to 2,5-dimethoxytoluene (produced by Tokyo Chemical Industry Co., Ltd.), and consequently the photoelectric conversion efficiency ($\eta$) was 8.50%.

Example 9

A photovoltaic element was prepared and measured, and a photoelectric conversion efficiency calculated in the same manner as in Example 1 except for changing 2,3-dihydrobenzofuran to 1,2,4-trimethoxybenzene (produced by Tokyo Chemical Industry Co., Ltd.), and consequently the photoelectric conversion efficiency ($\eta$) was 8.34%.

Example 10

A photovoltaic element was prepared and measured, and a photoelectric conversion efficiency calculated in the same manner as in Example 1 except for changing 2,3-dihydrobenzofuran to 3,4,5-trimethoxytoluene (produced by Tokyo Chemical Industry Co., Ltd., it has a melting point of 25° C., and it is melted and used if it is a solid matter in the atmosphere), and consequently the photoelectric conversion efficiency ($\eta$) was 8.61%.

Example 11

A photovoltaic element was prepared and measured, and a photoelectric conversion efficiency calculated in the same manner as in Example 1 except for changing 2,3-dihydrobenzofuran to 2,4,6-trimethoxytoluene (produced by Alfa-Aesar GmbH&Co.), and consequently the photoelectric conversion efficiency ($\eta$) was 8.50%.

Example 12

A photovoltaic element was prepared and measured, and a photoelectric conversion efficiency calculated in the same manner as in Example 1 except for changing 2,3-dihydrobenzofuran to $\alpha$-tetralone (produced by Tokyo Chemical Industry Co., Ltd.), and consequently the photoelectric conversion efficiency ($\eta$) was 8.10%.

Example 13

A photovoltaic element was prepared and measured, and a photoelectric conversion efficiency calculated in the same manner as in Example 1 except for changing 0.2 ml of a chloroform solution containing 2,3-dihydrobenzofuran in an amount of 2% by mass to 0.2 ml of a chloroform solution containing 1,2,3,5-tetramethoxybenzene (produced by Aldrich Chemical Co.) in an amount of 5% by mass, and consequently the photoelectric conversion efficiency ($\eta$) was 8.26%.

Example 14

A photovoltaic element was prepared and measured, and a photoelectric conversion efficiency calculated in the same manner as in Example 1 except for changing 0.2 ml of a chloroform solution containing 2,3-dihydrobenzofuran in an amount of 2% by mass to 0.2 ml of a chloroform solution containing 4-(methylthio)toluene (produced by Tokyo Chemical Industry Co., Ltd.) in an amount of 5% by mass, and consequently the photoelectric conversion efficiency ($\eta$) was 7.67%.

Example 15

A photovoltaic element was prepared and measured, and a photoelectric conversion efficiency calculated in the same manner as in Example 1 except for changing 0.2 ml of a chloroform solution containing 2,3-dihydrobenzofuran in an amount of 2% by mass to 0.2 ml of a chloroform solution containing 2-methoxythioanisole (produced by Tokyo Chemical Industry Co., Ltd.) in an amount of 5% by mass, and consequently the photoelectric conversion efficiency ($\eta$) was 8.36%.

Example 16

A photovoltaic element was prepared and measured, and a photoelectric conversion efficiency calculated in the same manner as in Example 1 except for changing 0.2 ml of a chloroform solution containing 2,3-dihydrobenzofuran in an amount of 2% by mass to 0.2 ml of a chloroform solution containing thioanisole (produced by Tokyo Chemical Industry Co., Ltd.) in an amount of 5% by mass, and consequently the photoelectric conversion efficiency ($\eta$) was 8.45%.

Example 17

A photovoltaic element was prepared and measured, and a photoelectric conversion efficiency calculated in the same manner as in Example 1 except for changing 0.2 ml of a chloroform solution containing 2,3-dihydrobenzofuran in an amount of 2% by mass to 0.2 ml of a chloroform solution containing ethyl phenyl sulfide (produced by Tokyo Chemical Industry Co., Ltd.) in an amount of 5% by mass, and consequently the photoelectric conversion efficiency ($\eta$) was 8.27%.

Example 18

A chlorobenzene solution (0.1 ml) (produced by Wako Pure Chemical Industries, Ltd.) containing 3,4,5-trimethoxytoluene (produced by Tokyo Chemical Industry Co., Ltd.) in an amount of 5% by mass, was added to a sample bottle containing 0.9 mg of A-1 and 1.1 mg of [70]PCBM (produced by Solenn Co., Ltd.), and further this was irradiated with ultrasonic waves for 30 minutes in an ultrasonic cleaning machine (US-2 manufactured by Iuchi Seieido Co., Ltd., output 120 W) to obtain a solution B. A photovoltaic element was prepared and measured, and a photoelectric conversion efficiency was calculated in the same manner as in Example 1 except for using the solution B in place of the solution A, and consequently the photoelectric conversion efficiency (η) was 8.31%.

Example 19

An o-dichlorobenzene solvent (0.1 ml) (produced by Wako Pure Chemical Industries, Ltd.) containing 3,4,5-trimethoxytoluene (produced by Tokyo Chemical Industry Co., Ltd.) in an amount of 5% by mass, was added to a sample bottle containing 1.35 mg of A-1 and 1.65 mg of [70]PCBM (produced by Solenn Co., Ltd.), and this was irradiated with ultrasonic waves for 30 minutes in an ultrasonic cleaning machine (US-2 manufactured by Iuchi Seieido Co., Ltd., output 120 W) to obtain a solution C. A photovoltaic element was prepared and measured, and a photoelectric conversion efficiency calculated in the same manner as in Example 1 except for using the solution C in place of the solution A, and consequently the photoelectric conversion efficiency (η) was 8.30%.

Example 20

A toluene solvent (0.1 ml) (produced by Nacalai Tesque Inc.) containing 3,4,5-trimethoxytoluene (produced by Tokyo Chemical Industry Co., Ltd.) in an amount of 5% by mass, was added to a sample bottle containing 0.9 mg of A-1 and 1.1 mg of [70]PCBM (produced by Solenn Co., Ltd.), and this was irradiated with ultrasonic waves for 30 minutes in an ultrasonic cleaning machine (US-2 manufactured by Iuchi Seieido Co., Ltd., output 120 W) to obtain a solution D. A photovoltaic element was prepared and measured, and a photoelectric conversion efficiency calculated in the same manner as in Example 1 except for using the solution D in place of the solution A, and consequently the photoelectric conversion efficiency (η) was 8.21%.

Example 21

An o-xylene solvent (0.1 ml) (produced by Tokyo Chemical Industry Co., Ltd.) containing 3,4,5-trimethoxytoluene (produced by Tokyo Chemical Industry Co., Ltd.) in an amount of 5% by mass, was added to a sample bottle containing 0.9 mg of A-1 and 1.1 mg of [70]PCBM (produced by Solenn Co., Ltd.), and this was irradiated with ultrasonic waves for 30 minutes in an ultrasonic cleaning machine (US-2 manufactured by Iuchi Seieido Co., Ltd., output 120 W) to obtain a solution E. A photovoltaic element was prepared and measured, and a photoelectric conversion efficiency calculated in the same manner as in Example 1 except for using the solution E in place of the solution A, and consequently the photoelectric conversion efficiency (η) was 8.03%.

Example 22

A 1,3,5-trimethylbenzene solvent (0.1 ml) (produced by Tokyo Chemical Industry Co., Ltd.) containing 3,4,5-trimethoxytoluene (produced by Tokyo Chemical Industry Co., Ltd.) in an amount of 5% by mass, was added to a sample bottle containing 1.35 mg of A-1 and 1.65 mg of [70]PCBM (produced by Solenn Co., Ltd.), and this was irradiated with ultrasonic waves for 30 minutes in an ultrasonic cleaning machine (US-2 manufactured by Iuchi Seieido Co., Ltd., output 120 W) to obtain a solution F. A photovoltaic element was prepared and measured, and a photoelectric conversion efficiency calculated in the same manner as in Example 1 except for using the solution F in place of the solution A, and consequently the photoelectric conversion efficiency (η) was 7.80%.

Comparative Example 1

A photovoltaic element was prepared and measured, and a photoelectric conversion efficiency was calculated in the same manner as in Example 1 except for not using 2,3-dihydrobenzofuran, and consequently the photoelectric conversion efficiency (η) was 4.45%.

Comparative Example 2

A photovoltaic element was prepared and measured, and a photoelectric conversion efficiency calculated in the same manner as in Example 1 except that 2,3-dihydrobenzofuran was changed to 1,8-diiodooctane (produced by Tokyo Chemical Industry Co., Ltd.) and heating/drying was changed to drying under reduced pressure, and consequently the photoelectric conversion efficiency (η) was 8.31%.

Comparative Example 3

A photovoltaic element was prepared and measured, and a photoelectric conversion efficiency calculated in the same manner as in Example 1 except for changing 2,3-dihydrobenzofuran to toluene (produced by Tokyo Chemical Industry Co., Ltd.), and consequently the photoelectric conversion efficiency (η) was 2.78%.

Comparative Example 4

A photovoltaic element was prepared and measured, and a photoelectric conversion efficiency calculated in the same manner as in Example 1 except for changing 2,3-dihydrobenzofuran to anisole (produced by Tokyo Chemical Industry Co., Ltd.), and consequently the photoelectric conversion efficiency (η) was 2.78%.

Comparative Example 5

A photovoltaic element was prepared and measured, and a photoelectric conversion efficiency calculated in the same manner as in Example 1 except for changing 2,3-dihydrobenzofuran to 1,2,3,4-tetrahydronaphthalene (produced by Tokyo Chemical Industry Co., Ltd.), and consequently the photoelectric conversion efficiency (η) was 6.93%.

Comparative Example 6

A photovoltaic element was prepared and measured, and a photoelectric conversion efficiency calculated in the same manner as in Example 1 except for changing 2,3-dihydrobenzofuran to indane (produced by Tokyo Chemical Industry Co., Ltd.), and consequently the photoelectric conversion efficiency (η) was 5.19%.

Comparative Example 7

A photovoltaic element was prepared and measured, and a photoelectric conversion efficiency calculated in the same manner as in Example 1 except for changing 2,3-dihydrobenzofuran to 1-methylnaphthalene (produced by Tokyo Chemical Industry Co., Ltd.), and consequently the photoelectric conversion efficiency (η) was 6.27%.

Example 23

A photovoltaic element prepared in the same manner as in Example 10 except that the bathocuproine of 5 nm and the lithium fluoride layer of 0.1 nm were changed to E-1 and an E-1 layer formed by vapor deposition with a thickness of 5 nm by a resistive heating method using a vacuum vapor deposition apparatus, was transferred into a glove box in a nitrogen atmosphere, and a glass plate was bonded to a side of the photovoltaic element using an epoxy resin to seal the photovoltaic element.

The upper and lower electrodes of the photovoltaic element thus prepared were connected to a 2400 series SourceMeter manufactured by TFF Corporation Keithley Instruments, and the element irradiated with simulated solar light (OTENTO-SUNIII manufactured by Bunkoukeiki Co., Ltd., spectral-shape: AM 1.5, intensity: 100 mW/cm$^2$) from the ITO layer side in the atmosphere, and the current value was measured, with the applied voltage being varied from −1 V to +2 V. Measurement was carried out immediately after the start of light irradiation and after 24 hours in a row of light irradiation. A photoelectric conversion efficiency (η) was calculated from the resulting current values, and consequently a retention rate of a photoelectric conversion efficiency after 24 hours of light irradiation was 76%.

Comparative Example 8

A photovoltaic element prepared in the same manner as in Comparative Example 2 except that the bathocuproine of 5 nm and the lithium fluoride layer of 0.1 nm were changed to E-1 and an E-1 layer was formed by vapor deposition with a thickness of 5 nm by a resistive heating method using a vacuum vapor deposition apparatus, was transferred into a glove box in a nitrogen atmosphere, and a glass plate bonded to a side of the photovoltaic element using an epoxy resin to seal the photovoltaic element.

The upper and lower electrodes of the photovoltaic element thus prepared were connected to a 2400 series SourceMeter manufactured by TFF Corporation Keithley Instruments, and the element was irradiated with simulated solar light (OTENTO-SUNIII manufactured by Bunkoukeiki Co., Ltd., spectral-shape: AM 1.5, intensity: 100 mW/cm$^2$) from the ITO layer side in the atmosphere, and the current value was measured, with the applied voltage being varied from −1 V to +2 V. Measurement was carried out immediately after the start of light irradiation and after 24 hours in a row of light irradiation. A photoelectric conversion efficiency (η) was calculated from the resulting current values, and consequently a retention rate of a photoelectric conversion efficiency after 24 hours of light irradiation was 27%.

Analysis Example 1

A chloroform solution (1.0 ml) containing 3,4,5-trimethoxytoluene in an amount of 5% by mass was added to a sample bottle containing 9 mg of A-1 and 11 mg of [70]PCBM, and further this was irradiated with ultrasonic waves for 30 minutes in an ultrasonic cleaning machine to obtain a solution B.

The solution B was drop-cast on a glass substrate, vacuum dried and then subjected to heating/drying at 100° C. for 30 minutes in a nitrogen atmosphere. The resulting film was scraped off, and an additive (3,4,5-trimethoxytoluene) remaining in the film was quantified using a purge & trap-gas chromatography-mass spectrometry method, and consequently the additive was contained in an amount of 0.094% by mass. We confirmed from this that sometimes an additive remained slightly and contained in a photoelectric conversion layer formed by drying our composition.

TABLE 1

| | Solvent | | Additive | | | | | | | |
|---|---|---|---|---|---|---|---|---|---|---|
| | Name | Boiling Point | Name | General Formula | Structural Formula | Boiling Point | Isc (mA/cm$^2$) | Voc (V) | FF | η (%) |
| Example 1 | chloroform | 61° C. | 2,3-dihydrobenzofuran | (1) | 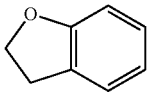 | 189° C. | 15.0 | 0.79 | 0.601 | 7.11 |
| Example 2 | | | 3,5-dimethylanisole | (1) | 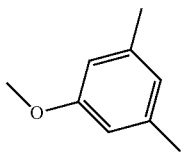 | 194° C. | 14.6 | 0.79 | 0.645 | 7.47 |
| Example 3 | | | 1-methoxynaphthalene | (2) | 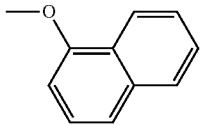 | 271° C. | 14.1 | 0.79 | 0.688 | 7.69 |
| Example 4 | | | 1,3-dimethoxybenzene | (1) | 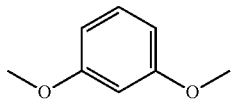 | 217° C. | 15.2 | 0.78 | 0.706 | 8.38 |

TABLE 1-continued

| | Solvent | | Additive | | | | Isc | Voc | | η |
|---|---|---|---|---|---|---|---|---|---|---|
| | Name | Boiling Point | Name | General Formula | Structural Formula | Boiling Point | (mA/cm²) | (V) | FF | (%) |
| Example 5 | | | 1,2-dimethoxybenzene | (1) | 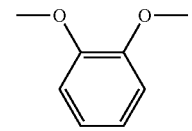 | 207° C. | 15.2 | 0.77 | 0.691 | 8.10 |
| Example 6 | | | 1,4-benzodioxane | (1) | 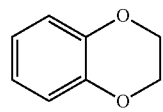 | 216° C. | 15.8 | 0.78 | 0.686 | 8.47 |
| Example 7 | | | 3,4-dimethoxytoluene | (1) | 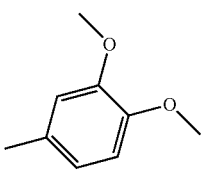 | 135° C./ 50 mmHg | 15.2 | 0.78 | 0.713 | 8.43 |
| Example 8 | | | 2,5-dimethoxytoluene | (1) | 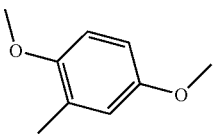 | 218° C. | 15.6 | 0.78 | 0.697 | 8.50 |
| Example 9 | | | 1,2,4-trimethoxybenzene | (1) | 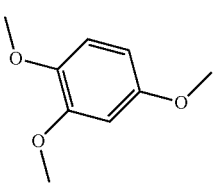 | 247° C. | 15.0 | 0.78 | 0.714 | 8.34 |
| Example 10 | | | 3,4,5-trimethoxytoluene | (1) | 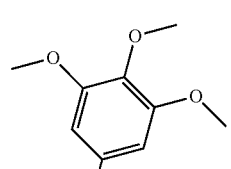 | 118° C./ 5 mmHg | 15.5 | 0.78 | 0.714 | 8.61 |
| Example 11 | | | 2,4,6-trimethoxytoluene | (1) | 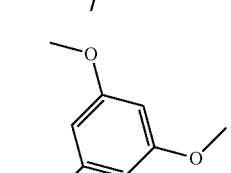 | 105° C./ 1 mmHg | 15.5 | 0.77 | 0.712 | 8.50 |
| Example 12 | | | α-tetralone | (1) | 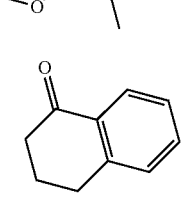 | 257° C. | 14.9 | 0.78 | 0.698 | 8.10 |
| Example 13 | | | 1,2,3,5-tetramethoxybenzene | (1) | 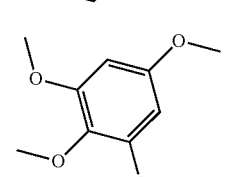 | >247° C. | 15.0 | 0.79 | 0.697 | 8.26 |

TABLE 1-continued

| | Solvent | | Additive | | | | Isc (mA/cm²) | Voc (V) | FF | η (%) |
|---|---|---|---|---|---|---|---|---|---|---|
| | Name | Boiling Point | Name | General Formula | Structural Formula | Boiling Point | | | | |
| Example 14 | | | 4-(methylthio)toluene | (3) | | 94° C./ 30.8 mmHg | 14.0 | 0.81 | 0.678 | 7.67 |
| Example 15 | | | 2-methoxythioanisole | (3) | | 142° C./ 25 mmHg | 15.1 | 0.8 | 0.693 | 8.36 |
| Example 16 | | | thioanisole | (3) | | 188° C. | 14.9 | 0.81 | 0.700 | 8.45 |
| Example 17 | | | ethyl phenyl sulfide | (3) | | 205° C. | 14.6 | 0.81 | 0.700 | 8.27 |
| Comparative Example 1 | | | — | | | — | 12.6 | 0.82 | 0.430 | 4.45 |
| Comparative Example 2 | | | 1,8-diiodooctane | — | | 144° C./ 2 mmHg | 15.0 | 0.76 | 0.727 | 8.31 |
| Comparative Example 3 | | | toluene | — | | 110° C. | 8.6 | 0.77 | 0.418 | 2.78 |
| Comparative Example 4 | | | anisole | — | | 157° C. | 8.9 | 0.75 | 0.418 | 2.78 |
| Comparative Example 5 | | | 1,2,3,4-tetrahydronaphthalene | — | | 208° C. | 13.9 | 0.78 | 0.640 | 6.93 |
| Comparative Example 6 | | | indane | — | | 179° C. | 14.3 | 0.62 | 0.584 | 5.19 |
| Comparative Example 7 | | | 1-methylnaphthalene | — | | 243° C. | 12.5 | 0.8 | 0.630 | 6.27 |

TABLE 2

| | Solvent | Boiling Point of Solvent | Additive | Boiling Point of Additive | Isc (mA/cm²) | Voc (V) | FF | η (%) |
|---|---|---|---|---|---|---|---|---|
| Example 18 | chlorobenzene | 131° C. | 3,4,5-trimethoxy-toluene | 118° C./ 5 mmHg | 15.6 | 0.77 | 0.692 | 8.31 |
| Example 19 | o-dichlorobenzene | 180° C. | | | 16.0 | 0.78 | 0.665 | 8.30 |
| Example 20 | Toluene | 110° C. | | | 15.4 | 0.75 | 0.709 | 8.21 |
| Example 21 | o-xylene | 144° C. | | | 15.5 | 0.78 | 0.663 | 8.03 |
| Example 22 | 1,3,5-trimethylbenzene | 165° C. | | | 15.1 | 0.79 | 0.654 | 7.80 |

TABLE 3

| | Solvent | Boiling Point of Solvent | Additive | Boiling Point of Additive | Retention Rate of Photoelectric Conversion Efficiency after 24 hours of Light Irradiation |
|---|---|---|---|---|---|
| Example 23 | chloroform | 61° C. | 3,4,5-trimethoxytoluene | 118° C./5 mmHg | 76% |
| Comparative Example 8 | chloroform | 61° C. | 1,8-diiodooctane | 144° C./2 mmHg | 27% |

Results of Examples and Comparative Examples are summarized in Tables 1 to 3. From comparisons between Examples 1 to 17 and Comparative Examples 1 and 2, it is found that according to our composition, a photovoltaic element characteristic of as high photoelectric conversion efficiency as 1,8-diiodooctane, is achieved.

The invention claimed is:

1. An organic semiconductor composition including an electron donating organic semiconductor, an electron accepting organic semiconductor, a solvent and an additive having a boiling point higher than that of the solvent, wherein the additive has a molecular weight of about 198 or below and is one or two or more compounds selected from the group consisting of compounds represented by any one of formulae (1) to (3):

(1)

(2)

(3)

in which in formula (1), A represents any aromatic hydrocarbon group having one ring or a heteroaromatic group having one ring, n is a natural number of 2 or more, $R_1$s are the only substituents coupled with the A, $R_1$s may be the same or different, and represent a methyl group, an alkoxy group or an alkanoyl group, further, at least one among a plurality of $R_1$s is either an alkoxy group or an alkanoyl group, and where a plurality of $R_1$s may be combined with one another to form a ring, in which in formula (2), B represents any aromatic hydrocarbon group having two rings or a heteroaromatic group having two rings, n is 1, $R_2$s are the only substituents coupled with the B, $R_2$s may be the same or different, and represent an alkyl group, an alkoxy group, an alkanoyl group or a thioalkyl group, further, at least one among $R_2$s is any one of an alkoxy group, an alkanoyl group and a thioalkyl group, and in which in formula (3), C represents any aromatic hydrocarbon group having one ring or a heteroaromatic group having one ring, n is a natural number of 1 or more, $R_3$s are the only substituents coupled with the C, $R_3$s may be the same or different, and represent an alkyl group, an alkoxy group, an alkanoyl group or a thioalkyl group, further, at least one among $R_3$s is a thioalkyl group, and where a plurality of $R_3$s may be combined with one another to form a ring.

2. The organic semiconductor composition according to claim 1, wherein the additive is a compound in which A in formula (1) is a benzene ring, a compound in which B in formula (2) is a naphthalene ring, or a compound in which C in formula (3) is a benzene ring.

3. The organic semiconductor composition according to claim 1, wherein the additive is a compound in which two or more $R_1$s are an alkoxy group in formula (1) or a compound in which at least two $R_1$s are an alkanoyl group and an alkyl group and form a ring in formula (1).

4. The organic semiconductor composition according to claim 3, wherein the additive is a compound in which n is 3 or more and three or more $R_1$s are an alkoxy group in formula (1).

5. The organic semiconductor composition according to claim 4, wherein the electron accepting organic semiconductor is a fullerene compound.

6. The organic semiconductor composition according to claim 3, wherein the electron accepting organic semiconductor is a fullerene compound.

7. The organic semiconductor composition according to claim 2, wherein the additive is a compound in which two or more $R_1$s are an alkoxy group in formula (1) or a compound in which at least two $R_1$s are an alkanoyl group and an alkyl group and form a ring in formula (1).

8. The organic semiconductor composition according to claim 2, wherein the additive is a compound in which n is 1 and $R_3$ is a thioalkyl group in formula (3).

9. The organic semiconductor composition according to claim 2, wherein the additive is a compound in which n is 2 or more and at least one of $R_3$s is an alkoxy group in formula (3).

10. The organic semiconductor composition according to claim 2, wherein the electron accepting organic semiconductor is a fullerene compound.

11. The organic semiconductor composition according to claim 1, wherein the additive is a compound in which n is 1 and $R_3$ is a thioalkyl group in formula (3).

12. The organic semiconductor composition according to claim 11, wherein the electron accepting organic semiconductor is a fullerene compound.

13. The organic semiconductor composition according to claim 1, wherein the additive is a compound in which n is 2 or more and at least one of $R_3$s is an alkoxy group in formula (3).

14. The organic semiconductor composition according to claim 13, wherein the electron accepting organic semiconductor is a fullerene compound.

15. The organic semiconductor composition according to claim 1, wherein the electron accepting organic semiconductor is a fullerene compound.

16. The organic semiconductor composition according to claim 1, wherein the electron donating organic semiconductor includes a conjugated polymer having a skeleton represented by any one of formulae (4) to (6):

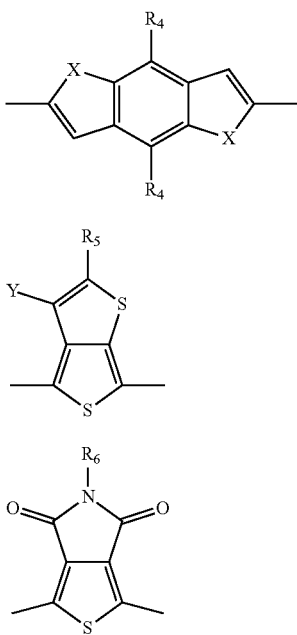

(4)

(5)

(6)

in which in formula (4), $R_4$s which may be the same or different represent an alkyl group, an alkoxy group, an optionally substituted heteroaryl group, an optionally substituted aryl group or a thioalkoxy group, and X which may be the same or different represents a sulfur atom, a selenium atom or an oxygen atom, in which in formula (5), $R_5$s represent an alkoxycarbonyl group or an alkanoyl group, and Y represents a hydrogen atom or a halogen atom, and in which in formula (6), $R_6$s represent an alkyl group, an optionally substituted heteroaryl group or an optionally substituted aryl group.

17. The organic semiconductor composition according to claim 16, wherein the conjugated polymer is a conjugated polymer represented by formula (7):

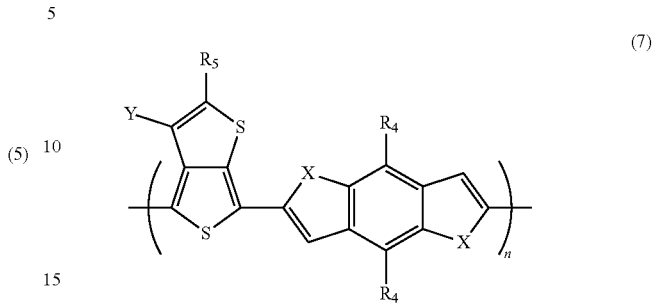

(7)

in which $R_4$s which may be the same or different represent an alkyl group, an alkoxy group, an optionally substituted heteroaryl group, an optionally substituted aryl group or a thioalkoxy group, $R_5$s represent an alkoxycarbonyl group or an alkanoyl group, X which may be the same or different represents a sulfur atom, a selenium atom or an oxygen atom, and Y represents a hydrogen atom or a halogen atom.

18. A photovoltaic element having an anode, a cathode and a photoelectric conversion layer formed by drying the organic semiconductor composition according to claim 1 which is formed between the anode and the cathode.

19. A photoelectric conversion device formed with the photovoltaic element according to claim 18.

20. A method of manufacturing a photovoltaic element having an anode, a cathode and a photoelectric conversion layer formed between the anode and the cathode, wherein the photoelectric conversion layer is formed by applying/drying the organic semiconductor composition according to claim 1.

* * * * *